(12) United States Patent
Houze et al.

(10) Patent No.: US 7,511,043 B2
(45) Date of Patent: Mar. 31, 2009

(54) FXR MODULATORS

(75) Inventors: Jonathan Houze, San Mateo, CA (US); Sharon McKendry, San Francisco, CA (US); Joshua Gergely, San Francisco, CA (US); Yi Xia, South San Francisco, CA (US); Bei Shan, Redwood City, CA (US); Frank Kayser, San Francisco, CA (US)

(73) Assignee: Amgen Inc., Thousand Oaks, CA (US)

( * ) Notice: Subject to any disclaimer, the term of this patent is extended or adjusted under 35 U.S.C. 154(b) by 900 days.

(21) Appl. No.: 10/794,228

(22) Filed: Mar. 4, 2004

(65) Prior Publication Data

US 2004/0176426 A1 Sep. 9, 2004

Related U.S. Application Data

(62) Division of application No. 09/945,293, filed on Aug. 31, 2001, now Pat. No. 6,777,446.

(60) Provisional application No. 60/258,092, filed on Dec. 22, 2000, provisional application No. 60/230,585, filed on Sep. 5, 2000.

(51) Int. Cl.
*A61K 31/497* (2006.01)
*C07D 241/36* (2006.01)
(52) U.S. Cl. ...................... 514/252.1; 564/184; 544/353
(58) Field of Classification Search .............. 514/252.1; 544/353; 564/184
See application file for complete search history.

(56) References Cited

U.S. PATENT DOCUMENTS

| 5,470,982 A | 11/1995 | Angerbauer et al. |
| 6,906,057 B1 | 6/2005 | Forman et al. |
| 6,984,650 B2 | 1/2006 | Haffner et al. |

FOREIGN PATENT DOCUMENTS

| WO | WO 96/34851 A1 | 11/1996 |
| WO | WO 00/17159 A1 | 3/2000 |

OTHER PUBLICATIONS

Database Beilstein Registry No. 43660, Beilstein Institut zur Foerderung der Chmischen Wissenschaften, Frankfurt am Main, Germany, Abstract of Voegtle et al., *Chemische Berichte*. 112:899-907 (1979).

Database Beilstein Registry No. 6451663, Beilstein Institut zur Foerderung der Chmischen Wissenschaften, Frankfurt am Main, Germany, Abstract of Erne et al., *Helvetica Chimica Acta* 63(8):2264-2270 (1980).

Chiang et al., "Farnesoid X Receptor Responds to Bile Acids and Represses Cholesterol 7α-Hydroxylase Gene (CYP7A1) Transcription," *Journal of Biological Chemistry*, vol. 275(15):10918-10924, 2000.

Goodwin et al., "A Regulatory Cascade of the Nuclear Receptors FXR, SHP-1, and LRH-1 Represses Bile Acid Biosynthesis," *Molecular Cell*, vol. 6:517-526, 2000.

Moss et al., "Glossary of Class Names of Organic Compounds and Reactive Intermediates Based on Structure (IUPAC Recommendations 1995)," *Pure and Applied Chemistry*, vol. 67(8/9):1307-1375, 1995.

Tu et al., "FXR, A Bile Acid Receptor and Biological Sensor," *TCM*, vol. 10(1):30-35, 2000.

Urizar et al., "A Natural Product that Lowers Cholesterol as an Antagonist Ligand for FXR," *Science*, vol. 296:1703-1706, 2002.

Wang et al., "Endogenous Bile Acids are Ligands for the Nuclear Receptor FXR/BAR," *Molecular Cell*, vol. 3:543-553, 1999.

*Primary Examiner*—James O. Wilson
*Assistant Examiner*—Paul V. Ward
(74) *Attorney, Agent, or Firm*—Jones Day

(57) ABSTRACT

The present invention provides compounds, pharmaceutical compositions and methods that are useful in modulating the farnesoid X receptor (FXR). As FXR is involved in negatively controlling the expression level of cholesterol 7α-hydroxylase (cyp7a), the rate-limiting enzyme involved in the oxidative metabolism of cholesterol into bile acids, the compounds described herein find utility in treating diseases associated with abnormally high or low cholesterol levels. In certain aspects, the FXR modulators (e.g., antagonists) described herein block the negative feed-back downregulation of cyp7a expression produced by certain cholic acids, the endogenous ligands for FXR. Moreover, as FXR forms heterodimers with the retinoid X receptor (RXR) in some cell types, modulation of the level of FXR activity in cells has a wide range of effects on a variety of biological processes which are mediated by RXR or other RXR-interacting proteins such as PPARγ and PPARα. Thus, compounds described herein are useful in treating other biological activities such as obesity, diabetes, lipid associated disorders, cancer, inflammatory disorders, disorders involving a disrupted or dysfunctional epidermal barrier, and various other metabolic disorders.

8 Claims, 15 Drawing Sheets

1.2.13    1.2.14    1.2.15    1.2.16

1.2.17    1.2.18    1.2.19    1.2.20

1.2.21    1.2.22    1.2.23    1.2.24

1.3.35  1.3.36

1.3.37  1.3.38

3.1.1

3.1.2

3.1.3

3.1.4

3.1.5

3.1.6

3.1.7

3.1.8

3.1.9

3.1.10

3.1.11

3.1.12

3.1.13

3.1.14

3.1.15

3.1.16

3.1.17  3.1.18  3.1.19

3.1.20  3.1.21  3.1.22

3.1.23  3.1.24  3.1.25

3.1.26  3.1.27  3.1.28

3.1.29  3.1.30  3.1.31

3.2.1

3.2.2

3.2.3

3.2.4

3.2.5

3.2.6

3.2.7

3.2.8

3.2.9

3.2.10

3.2.11

3.2.12

3.2.13

3.2.14

3.2.15

3.3.16

3.3.17

3.3.18

3.3.19

3.4.20

3.4.21

3.4.22

3.4.23

3.4.23

4.1

4.2

4.3

4.4

4.5

4.6

4.7

4.8

4.9

4.10

4.11

4.12

4.13

4.14

4.15

4.16

4.17

4.18

4.19

4.20

4.21

4.22

4.23

4.24

4.25

5.1

5.2

5.3

5.4

5.5

5.6

5.7

5.8

FXR MODULATORS

CROSS-REFERENCE TO RELATED APPLICATIONS

The present application is a divisional application of U.S. patent application Ser. No. 09/945,293, filed Aug. 31, 2001, now U.S. Pat. No. 6,777,446, which application claims priority to U.S. Application Nos. 60/230,585, filed Sep. 5, 2000, and 60/258,092, filed Dec. 22, 2000, the teachings of which are both incorporated herein by reference.

BACKGROUND OF THE INVENTION

The farnesoid X receptor (FXR), the peroxisome proliferator-activated receptor α (PPARα), and the liver X receptor α (LXRα) are members of a superfamily of approximately 150 proteins that bind to cis-acting elements in the promoters of their target genes and modulate gene expression in response to hormone activators or ligands. For many of these receptors, the activators are known, while for others, termed "orphan receptors," the activators are unknown. Furthermore, some of these receptors bind to their target genes as dimers consisting of two molecules of the same receptor (homodimers), while others bind as dimers consisting of one molecule each of two different receptors (heterodimers). Prominent among the latter are nuclear receptors that require heterodimerization with the retinoid X receptor (RXR), as disclosed in Yu et al. *Cell* 67:1251-1266 (1991). Members of this group include the vitamin D receptor, the thyroid hormone receptor ($T_3R$), the retinoic acid receptor (RAR), FXR, the peroxisome proliferator-activated receptors (PPARs) and LXR α.

FXR was first reported by Forman and coworkers, Forman *Cell* 81:687-693 (1995). This receptor is a protein having a relative molecular mass (Mr) of approximately 54,000, and is a vertebrate transcription factor regulated by intracellular metabolites. The receptor is activated by certain farnesoids, i.e., farnesol, compounds derived from farnesol, and/or compounds similar in structure to farnesol. These farnesoids include farnesol, farnesal, farnesyl acetate, farnesoic acid, geranylgeraniol and juvenile hormone III.

FXR is a nuclear receptor thought to be involved in negatively controlling the expression level of cholesterol 7α-hydroxylase (cyp7a), the rate-limiting enzyme involved in the oxidative metabolism of cholesterol into bile acids. As such, modulators of FXR activity will find utility in diseases associated with abnormally high or low cholesterol levels. Of particular value will be FXR antagonists, which block the negative feedback downregulation of cyp7a expression produced by certain cholic acids, the endogenous ligands for FXR. FXR is also involved in controlling the synthesis of isoprenoid derivatives (including cholesterol), and the proliferation of certain types of cancerous cells, such as those derived from colon carcinomas. Additionally, since FXR forms heterodimers with RXR in some cell types, modulation of the level of FXR activity in a cell has a wide range of effects on a variety of biological processes which are mediated by RXR or other RXR-interacting proteins such as PPARγ and PPARα. These other biological activities include, among others, obesity, diabetes, lipid associated disorders, cancer, inflammatory disorders, disorders involving a disrupted or dysfunctional epidermal barrier, and various other metabolic disorders. Modulators of FXR, both agonists and antagonists, will find utility in treating one or more of these diseases.

PCT Publication No. WO 00/40965, which is incorporated herein by reference, describes methods and compositions that are useful for modulating cholesterol levels in a cell and methods for identifying compounds that can be tested for ability to modulate cholesterol levels in mammals. These methods involve analyzing the effect of a test compound on the binding of FXR to an FXR ligand. Such ligands include, for example, bile acids, coactivators, and corepressors. The methods and compositions involve modulating FXR-mediated expression of genes involved in cholesterol metabolism.

Despite the advances made by WO 00/40965, there is a need in the art for new FXR modulators, both antagonists and agonists, to be used for a variety of indications. The present invention remedies this and other needs.

SUMMARY OF THE INVENTION

Atherosclerosis is a leading cause of death, myocardial infarctions, strokes, peripheral vascular disease and cardiovascular disease. One of the major contributing factors to atherosclerosis is hypercholesteremia. By modulating FXR-mediated expression of genes, using FXR modulating compounds, it is possible to mitigate and thereby treat hypercholesterolemia.

The present invention provides compounds, pharmaceutical compositions and methods that modulate FXR. The invention also provides methods of using the compounds and compositions for the treatment of conditions and disorders mediated by FXR, such as atherosclerosis, diabetes, obesity, dyslipidemia, hypercholesterolemia, hypertension, hyperlipidemia and hyperlipoproteinemia, certain inflammatory conditions and cancer.

As such, in certain aspects, the present invention provides compounds of Formula I:

$$B^1\text{-}L^1\text{-}A^1\text{-}L^2\text{-}B^2 \qquad\qquad I$$

In Formula I, $A^1$ represents a divalent group selected from the following: alkylene, alkenylene, alkynylene, cycloalkylene, cycloalkenylene, arylene, heteroarylene, heterocycloalkylene, and heterocycloalkenylene, or $A^1$ represents a single or double bond linking $L^1$ and $L^2$.

$L^1$ and $L^2$ are each independently selected from the following group of divalent radicals: —O—, —S—, —N($R^1$)—, —C(O)—, —C(O)N($R^1$)—, —O-alkylene-; —S-alkylene-, —N($R^1$)-alkylene, —C(O)-alkylene, —C(O)N($R^1$)-alkylene, —C(O)—O-alkylene, alkylene, alkenylene, alkynylene, cycloalkylene, cycloalkenylene, arylene, heteroarylene, heterocycloalkylene, and heterocycloalkenylene.

$B^1$ and $B^2$ are each independently selected from the group: alkyl, cycloalkyl, cycloalkenyl, aryl, heteroaryl, heterocycloalkyl, and heterocycloalkenyl.

In some aspects, $L^1$ can be additionally linked to $B^1$ via a group $X^1$ to form a 5-9 member ring. In a similar manner, $L^2$ can be additionally linked to $B^2$ via a group $X^2$ to form a 5-9 member ring.

$X^1$ and $X^2$ are each independently selected from: a single bond, —O—, —S—, —N($R^2$)—, —C(O)—, —C(O)N ($R^2$)—, —O-alkylene, —S-alkylene, —N($R^2$)-alkylene, —C(O)-alkylene, —C(O)N($R^2$)-alkylene, and —C(O)—O-alkylene.

$R^1$ and $R^2$ are each independently selected from: hydrogen, alkyl, heteroalkyl, cycloalkyl, heterocycloalkyl, cycloalkenyl, heterocycloalkenyl, aryl, heteroaryl, arylalkyl, aryl(heteroalkyl), (heteroaryl)alkyl, or (heteroaryl)heteroalkyl.

In another aspect, the present invention provides FXR modulators of Formula II:

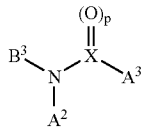

II

In Formula II, $A^2$ and $A^3$ are each independently selected from: alkyl, heteroalkyl, cycloalkyl, heterocycloalkyl, cycloalkenyl, heterocycloalkenyl, aryl, heteroaryl, arylalkyl, (heteroaryl)alkyl, aryl(heteroalkyl), or (heteroaryl)heteroalkyl.

$B^3$ is selected from the following: -hydrogen, -alkylene-C(O)$R^3$, —C(O)$R^3$, alkylene-C(O)N($R^3R^4$), —C(O)N($R^3R^4$), alkylene-S(O)$_n$N($R^3R^4$), —S(O)$_n$N($R^3R^4$), alkylene-N($R^3R^4$), alkylene-O$R^3$, and —C(O)O$R^3$.

$R^3$ and $R^4$ are each independently selected from: hydrogen, alkyl, heteroalkyl, cycloalkyl, heterocycloalkyl, cycloalkenyl, heterocycloalkenyl, aryl, heteroaryl, arylalkyl, (heteroaryl)alkyl, aryl(heteroalkyl), and (heteroaryl)heteroalkyl.

X is C, S, or N.

The subscript p is an integer from 0-2.

In still another embodiment, the present invention provides FXR modulators of Formula III:

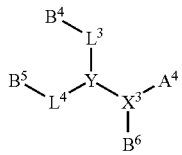

III

In Formula III, $A^4$ is selected from the following: —C(O)$R^5$, —C(O)N($R^5R^6$), —S(O)$_n$N($R^5R^6$), -alkylene-N($R^5R^6$), -alkylene-O$R^5$ and —C(O)O$R^5$.

$L^3$ and $L^4$ are each independently selected from the following divalent radicals: a single bond, —C(O)—, —S(O)$_p$—, and alkylene, wherein the subscript p is an integer from 0-2.

$B^4$, $B^5$ and $B^6$ are each independently selected from: alkyl, heteroalkyl, cycloalkyl, heterocycloalkyl, fused-benzoheterocycloalkyl, cycloalkenyl, heterocycloalkenyl, aryl, heteroaryl, arylalkyl, aryl(heteroalkyl), (heteroaryl)alkyl, and (heteroaryl)heteroalkyl.

Alternatively, $B^4$ and $B^5$ join to form a divalent arylene, heteroarylene, alkylene, or cycloalkylene linkage between $L^3$ and $L^4$.

$X^3$ and Y are each independently a trivalent nitrogen atom or a trivalent or tetravalent carbon atom.

$R^5$ and $R^6$ are each independently selected from: hydrogen, alkyl, heteroalkyl, cycloalkyl, heterocycloalkyl, cycloalkenyl, heterocycloalkenyl, aryl, heteroaryl, arylalkyl, aryl(heteroalkyl), (heteroaryl)alkyl, and (heteroaryl)heteroalkyl.

In still yet another aspect, the present invention provides FXR modulators of Formula IV:

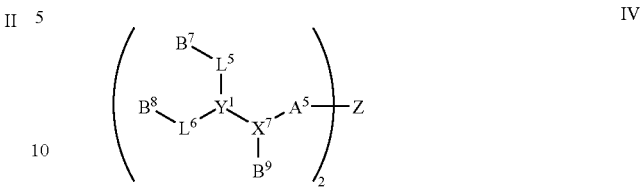

IV

In Formula IV, $A^5$ is selected from the following divalent linkages: —C(O)—, -alkylene-, —S(O)$_n$—, —C(O)N($R^{12}$)—, —S(O)$_2$N($R^{12}$)—, -alkylene-N($R^{12}$)—, -alkylene-O—, or —C(O)O—.

$L^5$ and $L^6$ are each independently selected from the following group of divalent radicals: a single bond, —C(O)—, —S(O)$_n$—, and alkylene, wherein the subscript n is an integer from 0-2.

$B^7$, $B^8$, and $B^9$ are each independently selected from: alkyl, heteroalkyl, cycloalkyl, heterocycloalkyl, benzoheterocycloalkyl, cycloalkenyl, heterocycloalkenyl, aryl, heteroaryl, arylalkyl, aryl(heteroalkyl), (heteroaryl)alkyl, and (heteroaryl)heteroalkyl.

Alternatively, $B^7$ and $B^8$ join to form a divalent arylene, heteroarylene, alkylene, or cycloalkylene linkage between $L^5$ and $L^6$.

Z is selected from the following divalent linkages: alkylene, heteroalkylene, cycloalkylene, or heterocycloalkylene.

$X^7$ and $Y^1$ are independently a trivalent nitrogen atom or a trivalent or tetravalent carbon atom; and $R^{12}$ is selected from: hydrogen, alkyl, heteroalkyl, cycloalkyl, heterocycloalkyl, cycloalkenyl, heterocycloalkenyl, aryl, heteroaryl, arylalkyl, aryl(heteroalkyl), (heteroaryl)alkyl, and (heteroaryl)heteroalkyl.

In yet another aspect, the present invention provides FXR modulators of Formula V:

V

In Formula V, $A^6$ and $A^7$ are each independently selected from: arylene, heteroarylene, cycloalkylene, or heterocycloalkylene.

$B^{10}$ represents: aryl, heteroaryl, arylalkyl, (heteroaryl)alkyl, alkyl, cycloalkyl, cycloalkenyl, heteroalkyl, heterocycloalkyl, or heterocycloalkenyl.

$L^7$ $L^8$ and $L^9$ are each independently selected from: —O—, —S—, —N($R^{13}$), —C(O)—, —S(O)—, —S(O)$_2$—, alkylene, —O-alkylene, —S-alkylene, —N($R^{13}$)-alkylene, —C(O)-alkylene, —C(O)N($R^{13}$)-alkylene, —C(O)—O-alkylene, a single bond, or a double bond, $X^8$ is selected from the following trivalent radicals: N, C$R^{13}$; and $R^{13}$ is selected from: hydrogen, alkyl, heteroalkyl, cycloalkyl, heterocycloalkyl, cycloalkenyl, heterocycloalkenyl, aryl, heteroaryl, arylalkyl, or (heteroaryl)alkyl.

Unless otherwise indicated, the compounds provided in the above formula are meant to include pharmaceutically acceptable salts and prodrugs thereof.

In addition to each of the aspect of the invention provided above, the present invention further provides pharmaceutical compositions containing one or more members of the classes of compounds above in admixture with a pharmaceutically acceptable carrier or excipient. Still further, the invention provides methods of using the compounds described herein for the treatment of FXR-mediated conditions and disorders as well as the modulation of cyp7a expression levels in mammals. FXR-mediated conditions and disorders include, but are not limited to, atherosclerosis, peripheral vascular disease, cardiovascular disease, hypercholesteremia, cholesterolemia, obesity, diabetes, inflammatory conditions and diseases associated with abnormally high or low cholesterol levels.

In other embodiments, the compounds of the present invention are administered in combination with certain other compounds of the present invention "in combination therapy" or in combination with other therapeutic compounds.

In yet another embodiment, the present invention provides the use of a compound of Formulae I-V for the manufacture of a medicament for treatment of an FXR mediated disease or condition.

These and other aspects will become more apparent when read with the accompanying diagram and detailed description, which follows.

DETAILED DESCRIPTION OF THE INVENTION AND PREFERRED EMBODIMENTS

Abbreviations and Definitions

Figure 1A:
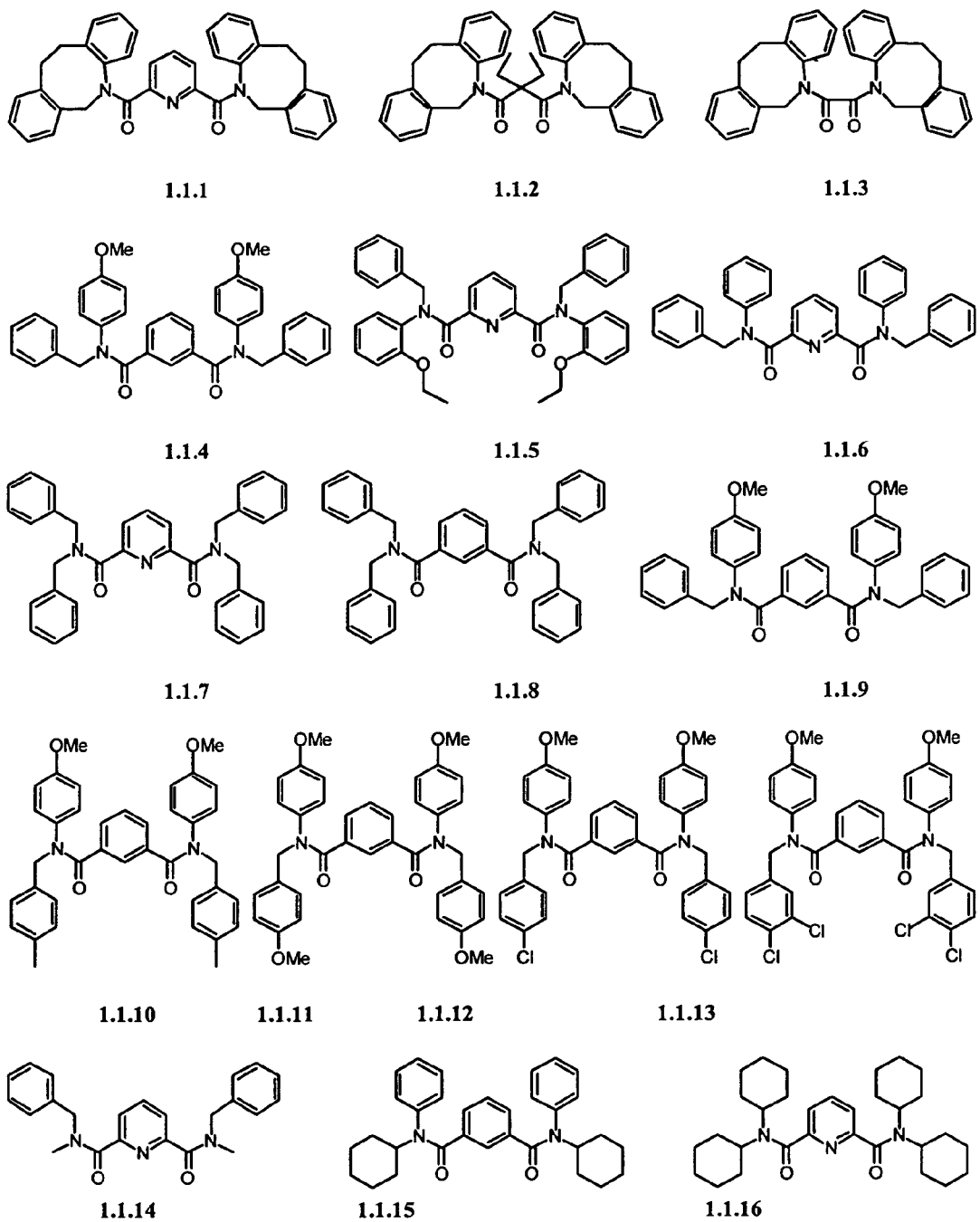
FIGS. 1(A-E) provide structures of compounds of Formula I.
Figure 1B:
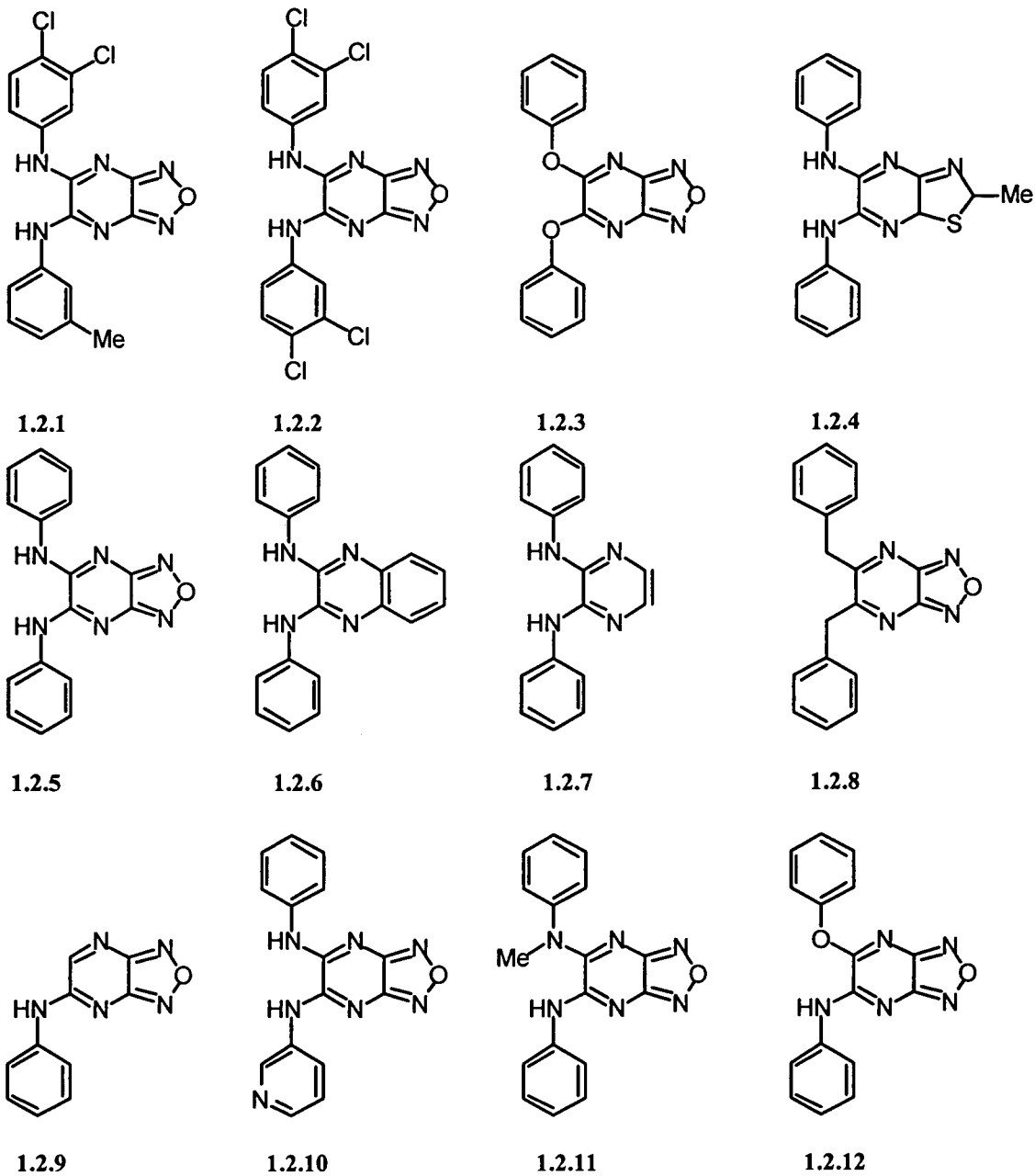

The abbreviations used herein are conventional, unless otherwise defined.

The term "modulate" or "modulation", as used herein in its various forms, refers to the ability of a compound to activate or inhibit the function of FXR, either directly or indirectly. Modulation may occur in vitro or in vivo. Modulation, as described herein, is intended to encompass antagonism, agonism, partial antagonism and/or partial agonism of a function or characteristic associated with FXR. Such compounds are FXR modulating compounds.

As used herein, the terms "treat", "treating" and "treatment" includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

As used herein, the term "FXR-mediated condition or disorder" and the like refers to a condition or disorder characterized by inappropriate, e.g., less than or greater than normal, FXR activity. Inappropriate FXR activity might arise as the result of FXR expression in cells which normally do not express FXR, increased FXR expression or decreased FXR expression (leading to, e.g., obesity or diabetes). Inappropriate FXR activity might also arise as the result of ligand secretion by cells which normally do not secrete an FXR ligand, increased FXR ligand expression or decreased FXR ligand expression. An FXR-mediated condition or disorder may be completely or partially mediated by inappropriate nuclear receptor activity. However, an FXR-mediated condition or disorder is one in which modulation of FXR results in some effect on the underlying condition or disease (e.g., an FXR antagonist results in some improvement in patient well-being in at least some patients).

As used herein, "obesity" refers to the excessive accumulation of body fat. Obesity may have genetic, environmental (e.g., expending less energy than is consumed) and regulatory determinants. Cardiovascular disorders, lipid disorders and metabolic disorders, such as hypertension, hyperlidemia, coronary artery disease and diabetes, are commonly associated with obesity.

As used herein, "diabetes" refers to type I diabetes mellitus juvenile onset diabetes, insulin dependent-diabetes mellitus or IDDM) or type II diabetes mellitus (non-insulin-dependent diabetes mellitus or NIDDM). The compounds, compositions and methods of the present invention preferably are used to treat NIDDM. NIDDM is characterized by insulin resistance and hyperglycemia. Obesity and lipid disorders are commonly associated with NIDDM.

"A therapeutically effective amount" refers to the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)ethyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "alkylene" by itself or as part of another substituent means a divalent radical derived from an alkane, as exemplified by —$CH_2CH_2CH_2CH_2$—. Typically, an alkylene group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "cycloalkylene" by itself or as part of another substituent means a divalent radical derived from an cycloalkane, as exemplified by cyclohexylene. Typically, an cycloalkylene group will have from 5-8 carbon atoms, with those groups having 6 carbon atoms being preferred in the present invention.

The term "alkenylene" by itself or as part of another substituent means a divalent radical derived from an alkenyl, as exemplified by —CH=CHCH$_2$CH$_2$—. Typically, alkenylene groups will have from 2 to 24 carbon atoms, with those groups having 10 or fewer carbon atoms being preferred in the present invention.

The term "alkynylene" by itself or as part of another substituent means a divalent radical derived from an alkynyl, as exemplified by —C≡CCH$_2$CH$_2$—. Typically, alkynylene groups will have from 2 to 24 carbon atoms, with those groups having 10 or fewer carbon atoms being preferred in the present invention.

The terms "alkoxy," "alkylamino" and "alkylthio" refer to those groups having an alkyl group attached to the remainder of the molecule through an oxygen, nitrogen or sulfur atom, respectively. Similarly, the term "dialkylamino" is used in a conventional sense to refer to —NR'R" wherein the R groups can be the same or different alkyl groups.

The term "heteroalkyl," by itself or in combination with another term, means, unless otherwise stated, a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$—S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Also included in the term "heteroalkyl" are those radicals described in more detail below as "heterocycloalkyl." The term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$CH$_2$—NH—CH$_2$—. For heteroalkylene groups, heteroatoms can also occupy either or both of the chain termini. Still further, for alkylene and heteroalkylene linking groups, no orientation of the linking group is implied.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like.

An "activated carbonyl" group is a carbonyl group whose electrophilicity is enhanced as a result of the groups attached to either side of the carbonyl. Examples of such activated carbonyl groups are (polyfluoroalkyl)ketones, (polyfluoroalkyl)aldehydes, alpha-keto esters, alpha-keto acids, alpha-keto amides, 1,2-diketones, 2-acylthiazoles, 2-acylimidazoles, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The term "heteroaryl" is meant to include those aryl rings which contain from zero to four heteroatoms selected from N, O, and S, wherein the nitrogen and sulfur atoms are optionally oxidized, and the nitrogen atom(s) are optionally quaternized. The "heteroaryl" groups can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group of acceptable substituents described below. The term "arylalkyl" is meant to include those radicals in which an aryl or heteroaryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', S(O)$_2$R', —S(O)$_2$NR'R", —CN and —NO$_2$ in a number ranging from zero to (2N+1), where N is the total number of carbon atoms in such radical. R', R" and R'" each independently refer to hydrogen, unsubstituted (C$_1$-C$_8$)alkyl and heteroalkyl, unsubstituted aryl, aryl substituted with 1-3 halogens, unsubstituted alkyl, alkoxy or thioalkoxy groups, or aryl-($C_1$-$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similarly, substituents for the aryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)$_2$R', —NR'—C(O)NR"R"', —NH—C($NH_2$)=NH, —NR'C($NH_2$)=NH, —NH—C($NH_2$)=NR', —S(O)R', —S(O)$_2$R', —S(O)$_2$NR'R", —NR"—S(O)$_2$—R', —$N_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R"' are independently selected from hydrogen, ($C_1$-$C_8$)alkyl and heteroalkyl, unsubstituted aryl, (unsubstituted aryl)-($C_1$-$C_4$)alkyl, and (unsubstituted aryl)oxy-($C_1$-$C_4$)alkyl.

Two of the substituents on adjacent atoms of the aryl ring may optionally be replaced with a substituent of the formula -T-C(O)—($CH_2$)$_q$—U—, wherein T and U are independently —NH—, —O—, —$CH_2$— or a single bond, and the subscript q is an integer of from 0 to 2. Alternatively, two of the substituents on adjacent atoms of the aryl ring may optionally be replaced with a substituent of the formula -A-($CH_2$)$_r$—B—, wherein A and B are independently —$CH_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —($CH_2$)$_s$—X—($CH_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted ($C_1$-$C_6$) alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al. (1977) *J. Pharm. Sci.* 66:1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

Compounds

In one aspect, the present invention provides FXR modulators of Formula I:

I

In Formula I, $A^1$ represents a divalent group selected from the following: alkylene, alkenylene, alkynylene, cycloalkylene, cycloalkenylene, arylene, heteroarylene, heterocycloalkylene, and heterocycloalkenylene, or $A^1$ represents a single or double bond linking $L^1$ and $L^2$. Preferably, $A^1$ is ($C_1$-$C_8$)alkylene, arylene (e.g., phenylene) or heteroarylene or a single bond. More preferably, $A^1$ is ($C_1$-$C_6$)alkylene, phenylene or a divalent pyridine group. Even more preferably, $A^1$ is $(C_1-C_4)$alkylene, arylene, or a divalent pyridine group.

$L^1$ and $L^2$ are each independently selected from the following group of divalent radicals: —O—, —S—, —N($R^1$)—, —C(O)—, —C(O)N($R^1$)—, —O-alkylene-, —S-alkylene-, —N($R^1$)-alkylene, —C(O)-alkylene, —C(O)N($R^1$)-alkylene, —C(O)—O-alkylene, alkylene, alkenylene, alkynylene, cycloalkylene, cycloalkenylene, arylene, heteroarylene, heterocycloalkylene, and heterocycloalkenylene. In the above alkylene and alkylene-containing groups, the number of carbon atoms will typically be from one to eight, and preferably, one to four carbon atoms. Cycloalkylene and unsaturated forms thereof, will typically contain four to seven carbon atoms, with those containing five or six carbon atoms being preferred.

$B^1$ and $B^2$ are each independently selected from the group: alkyl, cycloalkyl, cycloalkenyl, aryl, heteroaryl, heterocycloalkyl, and heterocycloalkenyl.

In some aspects, $L^1$ can be additionally linked to $B^1$ via a group $X^1$ to form a 5-9 member ring. In a similar manner, $L^2$ can be additionally linked to $B^2$ via a group $X^2$ to form a 5-9 member ring. In preferred embodiments, $B^1$ and $B^2$ are independently selected from: $(C_1-C_8)$alkyl, $(C_5-C_8)$cycloalkyl, $(C_5-C_8)$cycloalkenyl, aryl, heteroaryl, aryl$(C_1-C_4)$alkyl, (heteroaryl)$(C_1-C_4)$alkyl, and a five to eight-membered heterocycloalkyl group. Preferably, $B^1$ and $B^2$ are each independently a substituted or unsubstituted phenyl group, a substituted or unsubstituted benzyl group or a $(C_5-C_8)$cycloalkyl group. In the most preferred embodiments, $B^1$ and $B^2$ are the same.

$R^1$ and $R^2$ are each independently selected from: hydrogen, alkyl, heteroalkyl, cycloalkyl, heterocycloalkyl, cycloalkenyl, heterocycloalkenyl, aryl, heteroaryl, arylalkyl, aryl(heteroalkyl), (heteroaryl)alkyl, or (heteroaryl)heteroalkyl. More preferably, $R^1$ and $R^2$ are each $(C_1-C_8)$alkyl, $(C_1-C_8)$heteroalkyl, $(C_1-C_8)$cycloalkyl, $(C_1-C_8)$heterocycloalkyl, aryl, heteroaryl, aryl$(C_1-C_4)$alkyl, or (heteroaryl)$(C_1-C_4)$alkyl. Still more preferably, $R^1$ and $R^2$ are substituted or unsubstituted phenyl group, a substituted or unsubstituted benzyl group, a $(C_5-C_8)$cycloalkyl group or a $(C_1-C_8)$alkyl group.

$X^1$ and $X^2$ are each independently selected from: a single bond, —O—, —S—, —N($R^2$)—, —C(O)—, —C(O)N($R^2$)—, —O-alkylene, —S-alkylene, —N($R^2$)-alkylene, —C(O)-alkylene, —C(O)N($R^2$)-alkylene, and —C(O)—O-alkylene. Preferably, $X^1$ and $X^2$ are each independently a $(C_1-C_8)$alkylene group, with $(C_1-C_3)$alkylene groups being more preferred.

In certain aspects, the preferred compounds of Formula I are those in which:

$A^1$ is $(C_1-C_8)$alkylene, arylene, heteroarylene or a single bond.

$L^1$ and $L^2$ are —C(O)— or —C(O)N($R^1$)—.

$R^1$ is $(C_5-C_8)$cycloalkyl, aryl, heteroaryl, aryl$(C^1-C_4)$alkyl, or (heteroaryl)$(C^1-C_4)$alkyl; and $B^1$ and $B^2$ are aryl, heteroaryl, aryl$(C_1-C_4)$alkyl, (heteroaryl)$(C_1-C_4)$alkyl, $(C_1-C_8)$alkyl, or $(C_5-C^8)$cycloalkyl.

In other aspects, preferred compounds of Formula I are those in which $A^1$ is $(C_1-C_8)$alkylene, phenylene, divalent pyridine or a single bond.

$L^1$ and $L^2$ are —C(O)— or —C(O)N($R^1$)—.

$R^1$ is substituted or unsubstituted $(C_5-C_8)$cycloalkyl, substituted or unsubstituted phenyl, substituted or unsubstituted benzyl, or $(C_1-C_8)$alkyl; and $B^1$ and $B^2$ are independently substituted or unsubstituted $(C_5-C_8)$cycloalkyl, substituted or unsubstituted phenyl, substituted or unsubstituted benzyl. More preferably, $B^1$ and $B^2$ are the same.

In yet other aspects, preferred compounds of Formula I are those in which:

$A^1$ is alkylene, arylene, heteroarylene or a single bond.

$L^1$ and $L^2$ are —C(O)N($R^1$)—.

$R^1$ is aryl, heteroaryl, arylalkyl, or (heteroaryl)alkyl.

$B^1$ and $B^2$ are each independently aryl, heteroaryl, arylalkyl, (heteroaryl)alkyl, alkyl, or cycloalkyl.

In another preferred aspect, compounds of Formula I are those in which:

$A^1$ is heteroarylene containing two fused rings.

$L^1$ and $L^2$ are —O—, —NH—, or —N($R^1$)—.

$R^1$ is alkyl or heteroalkyl; and $B^1$ and $B^2$ are aryl, heteroaryl, arylalkyl, (heteroaryl)alkyl, alkyl, or cycloalkyl. Compounds of Formula I act primarily as FXR antagonists, but in certain instances, the compounds act as FXR agonists. Preferred compounds of Formula I are set forth in FIGS. 1A-1E.

In another aspect, the present invention provides FXR modulators of Formula II:

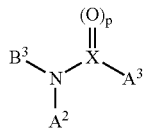

In Formula II, $A^2$ and $A^3$ are each independently selected from: alkyl, heteroalkyl, cycloalkyl, heterocycloalkyl, cycloalkenyl, heterocycloalkenyl, aryl, heteroaryl, arylalkyl, (heteroaryl)alkyl, aryl(heteroalkyl), or (heteroaryl)heteroalkyl.

$B^3$ is selected from the following: hydrogen, -alkylene-C(O)$R^3$, —C(O)$R^3$, alkyklene-C(O)N($R^3R^4$), —C(O)N($R^3R^4$), alkylene-S(O)$_n$N($R^3R^4$), —S(O)$_n$N($R^3R^4$), alkylene-N($R^3R^4$), alkylene-O$R^3$, and —C(O)O$R^3$.

$R^3$ and $R^4$ are each independently selected from: hydrogen, alkyl, heteroalkyl, cycloalkyl, heterocycloalkyl, cycloalkenyl, heterocycloalkenyl, aryl, heteroaryl, arylalkyl, (heteroaryl)alkyl, aryl(heteroalkyl), and (heteroaryl)heteroalkyl.

X is C, S, or N.

The subscripts n and p are each independently an integer from 0-2, provided that the following compound is excluded:

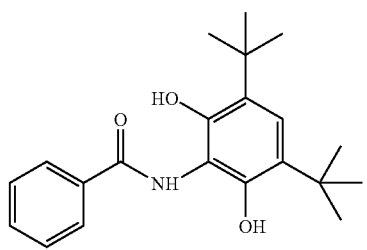

In one aspect, preferred compounds of Formula II are those in which: $A^2$ is an aryl group substituted ortho to the nitrogen with hydrogen bond donating groups including, but not limited to: —OH, —NH$_2$, —NHC(O)-alkyl, —NHSO$_2$-alkyl.

$A^3$ is aryl or heteroaryl.

$B^3$ is hydrogen.

X is C; and p is 1.

In another aspect, preferred compounds of Formula II are those in which:

$A^2$ and $A^3$ are aryl or heteroaryl.

$B^3$ is alkylene-C(O)N($R^3R^4$), or alkylene-S(O)$_n$N($R^3R^4$), wherein $R^3$ is arylalkyl or (heteroaryl)alkyl and $R^4$ is hydrogen X is S; and n is 2.

Compounds of Formula II act primarily as FXR antagonists, but in certain instances, act as FXR agonists. Preferred compounds of Formula II are set forth in FIGS. 2A-2-B.

In still another aspect, the present invention provides FXR modulators of Formula III:

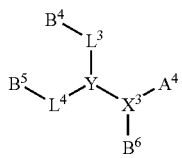

III

In Formula III, $A^4$ is selected from the following: hydrogen, —C(O)$R^5$, —C(O)N($R^5R^6$), —S(O)$_n$N($R^5R^6$), -alkylene-N($R^5R^6$), -alkylene-O$R^5$, and —C(O)O$R^5$.

$L^3$ and $L^4$ are each independently selected from the following divalent radicals: a single bond, —C(O)—, —S(O)$_p$—, and alkylene, wherein the subscript p is an integer from 0-2.

$B^4$, $B^5$ and $B^6$ are each independently selected from: hydrogen, alkyl, heteroalkyl, cycloalkyl, heterocycloalkyl, fused-benzoheterocycloalkyl, cycloalkenyl, heterocycloalkenyl, aryl, heteroaryl, arylalkyl, aryl(heteroalkyl), (heteroaryl)alkyl, and (heteroaryl)heteroalkyl.

Alternatively, $B^4$ and $B^5$ join to form a divalent arylene, heteroarylene, alkylene, or cycloalkylene linkage between $L^3$ and $L^4$, $B^6$ is hydrogen, alkyl, heteroalkyl, heterocycloalkyl, arylalkyl or (heteroaryl)alkyl.

$X^3$ and Y are independently a trivalent nitrogen atom or a trivalent or tetravalent carbon atom.

$R^5$ and $R^6$ are each independently selected from: hydrogen, alkyl, heteroalkyl, cycloalkyl, heterocycloalkyl, cycloalkenyl, heterocycloalkenyl, aryl, heteroaryl, arylalkyl, aryl(heteroalkyl), (heteroaryl)alkyl, and (heteroaryl)heteroalkyl.

In certain aspects, preferred compounds of Formula III are those in which $A^4$ is hydrogen, —C(O)N($R^5R^6$) or —S(O)$_2$N($R^5R^6$).

$R^5$ and $R^6$ are each independently alkyl, cycloalkyl, or heterocycloalkyl.

$L^3$ and $L^4$ are each independently —C(O)—, —S(O)$_2$—, or lower alkylene.

$B^4$ and $B^5$ join to form an arylene or heteroarylene linkage between $L^3$ and $L^4$.

X is tetravalent carbon in the R configuration.

Y is trivalent nitrogen; and $B^6$ is hydrogen, alkyl, heteroalkyl, heterocycloalkyl, arylalkyl, or (heteroaryl)alkyl.

In another preferred aspect, compounds of Formula III are those in which:

$A^4$ is hydrogen, —C(O)N($R^5R^6$) or —S(O)$_2$N($R^5R^6$).

$R^5$ and $R^6$ are each independently alkyl, cycloalkyl, or heterocycloalkyl.

$L^3$ and $L^4$ are independently —C(O)—, —S(O)$_2$—, or lower alkylene.

$B^4$ and $B^5$ are independently hydrogen, alkyl, arylalkyl, aryl, or heteroaryl.

X is tetravalent carbon in the R configuration.

Y is trivalent nitrogen; and $B^6$ is hydrogen, alkyl, heteroalkyl, heterocycloalkyl, arylalkyl, or (heteroaryl)alkyl. Compounds of Formula III act primarily as FXR antagonists, but in certain instances, act as FXR agonists. Preferred compounds of Formula III are set forth in FIGS. 3A-3D.

In another embodiment, the present invention provides compounds of Formula IIIa.

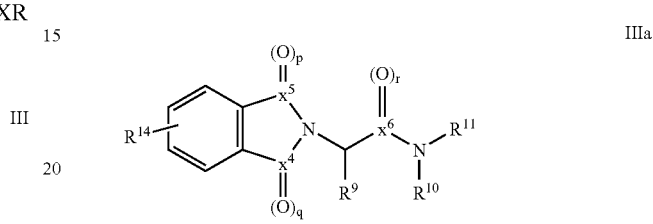

IIIa wherein:

$X^4$, $X^5$ and $X^6$ are each independently C or S.

$R^{10}$ and $R^{11}$ are each independently alkyl, cycloalkyl, or heterocycloalkyl.

$R^9$ is an optionally substituted aryl, heteroaryl, arylalkyl, (heteroaryl)alkyl, heterocycloalkyl; and the subscripts p, q, and r are each independently integers from 0-2.

$R^{14}$ is selected from hydrogen, halogen, alkyl, alkoxy, alkylamino, alkylthio, acyl, cycloalkyl and aryl.

In yet another embodiment, the present invention provides compounds of Formula IIIb.

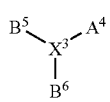

IIIb

In Formula IIIb, $A^4$ is selected from hydrogen, —C(O)$R^5$, —C(O)N($R^5R^6$), —S(O)$_n$N($R^5R^6$), -alkylene-N($R^5R^6$), -alkylene-O$R^5$ and —C(O)O$R^5$.

$B^5$ and $B^6$ are independently selected from hydrogen, alkyl, heteroalkyl, cycloalkyl, heterocycloalkyl, fused-benzoheterocycloalkyl, cycloalkenyl, heterocycloalkenyl, aryl, heteroaryl, arylalkyl, aryl(heteroalkyl), (heteroaryl)alkyl and (heteroaryl)heteroalkyl.

$X^3$ is a trivalent nitrogen atom or a trivalent or tetravalent carbon atom.

In still yet another aspect, the present invention provides FXR modulators of Formula IV:

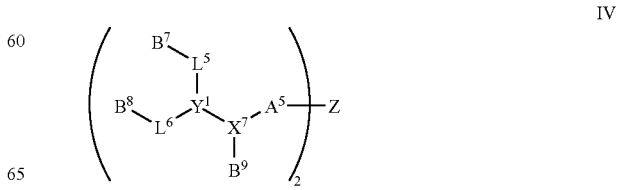

IV

In Formula IV, $A^5$ is selected from the following divalent linkages: —C(O)—, -alkylene-, —S(O)$_n$—, —C(O)N(R$^{12}$)—, —S(O)$_2$N(R$^{12}$)—, -alkylene-N(R$^{12}$)—, -alkylene-O—, or —C(O)O—.

$L^5$ and $L^6$ are each independently selected from the following group of divalent radicals: a single bond, —C(O)—, —S(O)$_n$—, and alkylene, wherein the subscript n is an integer from 0-2.

$B^7$, $B^8$, and $B^9$ are each independently selected from: alkyl, heteroalkyl, cycloalkyl, heterocycloalkyl, benzoheterocycloalkyl, cycloalkenyl, heterocycloalkenyl, aryl, heteroaryl, arylalkyl, aryl(heteroalkyl), (heteroaryl)alkyl, and (heteroaryl)heteroalkyl.

Alternatively, $B^7$ and $B^8$ join to form a divalent arylene, heteroarylene, alkylene, or cycloalkylene linkage between $L^5$ and $L^6$.

Z is selected from the following divalent linkages: alkylene, heteroalkylene, cycloalkylene, or heterocycloalkylene.

$X^7$ and $Y^1$ are independently a trivalent nitrogen atom or a trivalent or tetravalent carbon atom; and $R^{12}$ is selected from: hydrogen, alkyl, heteroalkyl, cycloalkyl, heterocycloalkyl, cycloalkenyl, heterocycloalkenyl, aryl, heteroaryl, arylalkyl, aryl(heteroalkyl), (heteroaryl)alkyl, and (heteroaryl)heteroalkyl.

In certain aspects, preferred compounds of Formula IV are those in which:

$A^5$ is —C(O)—, —C(O)N(R$^{12}$)— or —S(O)$_2$N(R$^{12}$)—.

$R^{12}$ is alkyl, cycloalkyl, or heterocycloalkyl.

$B^7$ and $B^8$ are combined in an arylene or heteroarylene linkage between $L^5$ and $L^6$.

$B^9$ is alkyl, heteroalkyl, heterocycloalkyl, arylalkyl, or (heteroaryl)alkyl.

Z is alkylene, heteroalkylene, or heterocycloalkylene.

$L^5$ and $L^6$ are independently —C(O)—, —S(O)$_2$—, or lower alkylene.

$X^7$ is tetravalent carbon; and $Y^1$ is trivalent nitrogen. Compounds of Formula IV act primarily as FXR antagonists, but some of the compounds act as FXR agonists. Preferred compounds of Formula IV are set forth in FIGS. 4A-4C.

In yet another aspect, the present invention provides novel FXR modulators of Formula V:

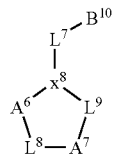

V

In Formula V, $A^6$ and $A^7$ are each independently selected from: arylene, heteroarylene, cycloalkylene, or heterocycloalkylene.

$B^{10}$ represents: aryl, heteroaryl, arylalkyl, (heteroaryl)alkyl, alkyl, cycloalkyl, cycloalkenyl, heteroalkyl, heterocycloalkyl, or heterocycloalkenyl.

$L^7$, $L^8$, and $L^9$ are each independently selected from: —O—, —S—, —N(R$^{13}$), —C(O)—, —S(O)—, —S(O)$_2$—, alkylene, —O-alkylene, —S-alkylene, —N(R$^{13}$)-alkylene, —C(O)—alkylene, —C(O)N(R$^1$)-alkylene, —C(O)—O-alkylene, a single bond, or a double bond;

$X^8$ is selected from the following trivalent radicals: N, CR$^{13}$; and $R^{13}$ is selected from: hydrogen, alkyl, heteroalkyl, cycloalkyl, heterocycloalkyl, cycloalkenyl, heterocycloalkenyl, aryl, heteroaryl, arylalkyl, or (heteroaryl)alkyl.

In certain aspects, $A^6$ and $A^7$ are aryl, heteroaryl, cycloalkyl, or heterocycloalkyl;

$B^{10}$ is aryl, heteroaryl, arylalkyl, or (heteroaryl)alkyl;

$L^7$ and $L^8$ are independently selected from —C(O)—, —S(O)—, or —S(O)$_2$—;

$L^9$ is —C(O)—, alkylene, or a single bond; and $X^5$ is N. Compounds of Formula V act primarily as FXR agonists, but in certain aspects act as FXR antagonists. Preferred compounds of Formula V are set forth in FIG. 5.

The vast majority of the compounds contemplated for use in the present invention are novel, while one or more of the specific compounds set forth in FIGS. 1-5 may be commercially available. The present invention specifically contemplates the exclusion, by way of proviso, of commercially available compounds from the compound claims (and, if appropriate, from the pharmaceutical composition claims). Unless otherwise indicated, it is to be understood that the present invention includes those compounds that are novel. The pharmaceutical compositions, various methods (e.g., methods of treating certain FXR-mediated conditions and disorders), and the like include both the novel compounds of the invention and compounds that are commercially available.

Synthetic Schemes

Illustrative synthetic methods for representative compounds in Formulae I-V are provided in the examples set forth below. One of skill in the art will appreciate that substitution of one starting material or reagent for another, will provide additional compounds within the scope of the present invention. For example, in Example I the synthesis of compound 1.1.4 is set forth. A skilled artisan will readily appreciate however, that isophthaloyl dichloride can be reacted with N-benzyl-p-anisidine as indicated, or it can be reacted with a variety of other substituted N-benzyl anilines.

In a similar manner, substitution of isophthaloyl dichloride with 2,6-pyridinedicarbonylchloride (commercially available from Aldrich Chemical Co., Milwaukee, Wis. USA) will provide compounds of Formula I wherein $A^1$ is a heteroarylene group. A number of symmetrical compounds of Formula I are provided in FIGS. 1A-1E. All of these compounds can be prepared by analogous amide bond-forming reactions using commercially available starting materials or materials that are readily available from established literature procedures.

Further examples of compounds of Formula I and their syntheses are set forth in Examples 2 and 3. In Example 3, a 2,3-dichloro-6-nitroquinoxaline is reacted with an excess (over two equivalents) of a substituted aniline to provide the target compound. Similarly, other substituted 2,3-dichloro-quinoxalines can be used with other substituted anilines, arylalkylamines or alkylamines. Unsymmetrically substituted compounds can be prepared as described for compound 1.2.26 of FIG. 1D, replacing 3,4-dimethylaniline with other substituted anilines and replacing cyclohexylamine with other alkylamines, cycloalkylamines, arylalkylamines and anilines.

A representative compound of Formula II is set forth in Example 4. As illustrated therein, N-(2,6-dihydoxy-phenyl)-benzamide was suspended in 85% $H_3PO_4$ and 2-methyl-2-propanol. The reaction mixture was vigorously stirred and then poured into of deionized water and extracted with ethyl acetate to generate compound 2.1.1 (see, FIG. 2A).

A further example of a compound of Formula II is shown in Example 5. As illustrated therein, N-(3-trifluoromethyl-phenyl)-benzenesulfonamide is dissolved in anhydrous THF and then treated with potassium tert-butoxide and a chloroacetamide. Thereafter, Bu$_4$NI was added to catalyze the alkylation reaction. After work up, compound 2.2.10 was produced in good yield. Those of skill in the art will appreciate that suitable modifications of Example 4 and 5 will generate further compounds of Formula II.

Likewise, compounds of Formula III can be prepared as set forth in Example 6, wherein the synthesis of compound 3.1.1 is illustrated. A skilled artisan will appreciate that by suitable modification of Example 6, as for example, replacing N-phthaloyl-DL-phenylalanine by a variety of N-phthaloyl-DL-amino acids, additional compounds of the invention can be generated. Dicyclohexylamine can also be replaced with other dicycloalkylamines, N-cylcoalkyl anilines, N-cycloalkyl N-benzylamines, and the like.

Compounds of Formula IV can be prepared using methods similar to those described in Example 8, wherein the synthesis of compound 4.7 is illustrated. In this example, N-substituted amino acids (N-benzyl, N-benzoyl, N-alkyl, N,N-dialkyl and the like) can be converted to amides of Formula IV by simple coupling reactions using, for example, dicyclohexylamine, isopropyl t-butyl amine, 3-pentyl t-butyl amine, and the like. Other examples of compounds of Formula IV are set forth in FIG. 4A-4C.

In addition, compounds of Formula V can be prepared using methods similar to those described in Example 9, wherein the synthesis of 5.3 is illustrated. As shown therein, an ortho-nitro diaryl sulfonamide (e.g., compound 5.3a in Example 9) can be converted to an ortho amino compound (see, for example, compound 5.3b in Example 9) then oxidized to a diazonium compound that undergoes an intramolecular C—H bond insertion on the nearby phenyl ring to form a tricyclic structure (e.g., 5.3c in Example 9). Sulfonylation of the sulfonamide nitrogen of 5.3c can be accomplished using standard conditions. Alternatively, the nitrogen can be acylated with, for example, benzoyl chloride or a substituted benzoyl chloride to form other compounds useful as FXR antagonists. For compounds that are symmetrical, N-phthaloyl amino acids can be reacted with, for example, diamines such as 1,6-hexanediamine, N,N'-dimethyl butanediamine, 4,13-diaza-18-crown-6,7,13-diaza-15-crown-5, N,N'-dimethyl 2-aminoethyl ether, 1,4-bis(aminomethyl)cyclohexane, and the like.

Compositions

In view of the FXR antagonism and in some cases, agonism effects of the compounds described herein, the present invention further provides pharmaceutical compositions comprising one or more of the above compounds in combination with a pharmaceutically acceptable carrier or excipient.

In one embodiment, the present invention provides the subject compounds combined with a pharmaceutically acceptable excipient such as sterile saline or other medium, water, gelatin, an oil, etc. to form pharmaceutically acceptable compositions. The compositions and/or compounds may be administered alone or in combination with any convenient carrier, diluent, etc. and such administration may be provided in single or multiple dosages. Useful carriers include, but are not limited to, solid, semi-solid or liquid media including water and non-toxic organic solvents.

In another embodiment, the present invention provides the subject compounds in the form of a prodrug, which can be metabolically or chemically converted to the subject compounds by the recipient host. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

The compositions can be provided in any convenient form, including tablets, capsules, lozenges, troches, hard candies, powders, sprays, creams, suppositories, etc. As such, the compositions, in pharmaceutically acceptable dosage units or in bulk, may be incorporated into a wide variety of containers. For example, dosage units may be included in a variety of containers including capsules, pills, etc.

The pharmaceutical compositions of the present invention are suitable for use in a variety of drug delivery systems. Examples of suitable formulations for use in the present invention are found in *Remington's Pharmaceutical Sciences* (Mack Publishing Company, Philadelphia, Pa., 17th ed. (1985)), which is incorporated herein by reference. In addition, for a brief review of methods for drug delivery, see, Langer, *Science* 249:1527-1533 (1990), which is incorporated herein by reference.

The pharmaceutical compositions of the present invention are intended for parenteral, topical, oral or local administration. In certain aspects, the pharmaceutical compositions are administered parenterally, e.g., intravenously, subcutaneously, intradermally, or intramuscularly. In one embodiment, the invention provides compositions for parenteral administration which comprise a compound of the present invention, dissolved or suspended in an acceptable carrier, preferably an aqueous carrier. A variety of aqueous carriers may be used including, for example, water, buffered water, 0.4% saline, 0.3% glycine, hyaluronic acid and the like. These compositions may be sterilized by conventional, well-known sterilization techniques or, they may be sterile filtered. The resulting aqueous solutions may be packaged for use as is or lyophilized, the lyophilized preparation being combined with a sterile solution prior to administration. The compositions may contain pharmaceutically acceptable auxiliary substances as required to approximate physiological conditions including pH adjusting and buffering agents, tonicity adjusting agents, wetting agents and the like, such as, for example, sodium acetate, sodium lactate, sodium chloride, potassium chloride, calcium chloride, sorbitan monolaurate, triethanolamine oleate, etc.

For solid formulations, compounds of the present invention can be admixed with conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed carriers or excipients, such as those carriers previously listed, and generally 10-95% of active ingredient and more preferably at a concentration of 25%-75%.

For aerosol administration, the compounds of the present invention and antidiabetic agents are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. Accordingly, the present invention also provides pharmaceutical compositions comprising a pharmaceutically acceptable carrier or excipient and either a compound of the present invention or a pharmaceutically acceptable salt. The present invention also contemplates the use of depot formulations.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is a finely divided solid that is in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

It will be appreciated that the actual preferred course of therapy will vary according to, inter alia, the mode of administration of the compound of the present invention, the particular formulation being utilized, the mode of administration of the compounds, the particular disease being treated and the particular host being treated. The optimal course of therapy for a given set of conditions can be ascertained by those skilled in the art using conventional course of therapy determination tests and in view of the information set out herein.

Methods and Uses, Dosages and Schedules

In another embodiment, the present invention provides methods of using the compounds and pharmaceutical compositions described herein for the treatment of FXR modulated diseases and conditions. In certain aspects, the compounds of the present invention that are administered comprise a compound of Formulae I-V formulated individually, together, or with one or more additional active agents. In other embodiments, the present invention provides the use of a compound of Formulae I-V for the manufacture of a medicament for treatment of an FXR mediated disease or condition.

In therapeutic use for the treatment of obesity, atherosclerosis, peripheral vascular disease, hypercholesteremia, diabetes, or inflammatory conditions, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages that are less than the optimum dose of the compound. Thereafter, the dosage is increased by small increments until the optimum effect under circumstances is reached. For convenience, the total daily dosage may be divided and administered in portions during the day, if desired.

In therapeutic applications, the compounds of the present invention are administered to a patient in a amount sufficient to elicit a response. An amount adequate to accomplish this is defined as "therapeutically effective combination dose."

Effective combination amounts for various uses will depend on, for example, the particular compound of the present invention employed, the manner of administration, the weight and general state of health of the patient, and the judgment of the prescribing physician. In one embodiment, the composition or formulation to be administered will contain a quantity of a compound(s) according to Formulae I-V in an amount effective to treat the disease/condition of the subject being treated.

In certain instances, administration of the compounds of the present invention can be via any method, which provides systemic exposure to the compound of this invention, preferably to the muscle and fatty tissue. These methods include oral routes, parenteral, intraduodenal routes, etc. Generally, the compounds of the present invention are administered in single (e.g., once daily) or multiple doses. The compounds of the present invention are generally administered in the form of a pharmaceutical composition comprising at least one of the compounds of Formulae I-V together with a pharmaceutically acceptable carrier or diluent. Thus, the compounds of this invention can be administered individually or together in any conventional oral, parenteral or transdermal dosage form.

For oral administration, a pharmaceutical composition can take the form of solutions, suspensions, tablets, pills, capsules, powders, and the like. Tablets containing various excipients such as sodium citrate, calcium carbonate and calcium phosphate are employed along with various binders such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compounds of this invention can be combined with various sweetening agents, flavoring agents, coloring agents, emulsifying agents and/or suspending agents, as well as such diluents as water, ethanol, propylene glycol, glycerin and various like combinations thereof.

In other aspects, the compounds and methods of the present invention are useful in treating various skin conditions and skin ailments. Skin conditions that are treatable by the compounds of this invention include, but are not limited to, the skin of premature infants of gestational age less than 33 weeks; atopic and seborrheic dermatitis; inflammation to mucous membranes, such as cheilitis, chapped lips, nasal irritation and vulvovaginitis; eczematous dermatitis resulting from allergic and irritant contact, eczema craquelee, radiation and stasis dermatitis; ulcers and erosions due to chemical or thermal burns, bullous disorders, or vascular compromise or ischemia including venous, arterial, embolic or diabetic ulcers; ichthyoses; with or without an associated barrier abnormality; epidermolysis bullosa; psoriasis; hypertrophic scars and keloids; intrinsic aging and/or dermatoheliosis; mechanical friction blistering; corticosteroid atrophy; and melanoma and non-melanoma skin cancer, including lignin melanoma, basal cell carcinoma, squamous cell carcinoma, actinic keratoses, and virally induced neoplasia (warts and condylomata accuminata) (see, U.S. Pat. No. 6,060,515, incorporated herein by reference).

In certain embodiments, the compounds of the present invention are administered in combination with certain other compounds of the present invention "in combination therapy" or in combination with other therapeutic compounds. In this aspect, an amount adequate to accomplish this, i.e., elicit a response, is defined as "a therapeutically effective combination dose." The term "simultaneous manner" and "combination treatment" refer to an administration protocol wherein the compound of the present invention (e.g., compound of Formula I) and at least one other therapeutic compound (e.g., compound of Formula III, or other therapeutic agent) are administered within a single period of time. The time period can be measured in hours (e.g., 24 hours) or days (e.g., 30 days).

"A combination amount sufficient," "an effective combination amount" "therapeutically effective combination amount" or "an effective amount of the combination of" all refer to a combined amount of both a compound of the present invention (e.g., compound of Formula I) and another therapeutic compound (e.g., compound of Formula II) or other therapeutic agent, that is effective to ameliorate symptoms associated with FXR-mediated diseases. As used herein, the term "combination" means that at least the two compounds can be delivered in a simultaneous manner, in combination therapy wherein the first compound is administered first, followed by the second compound, as well as wherein the second compound is delivered first, followed by the first compound. The desired result can be either a subjective relief of a symptom(s) or an objectively identifiable improvement in the recipient of the dosage.

In certain preferred aspects, the present invention provides combination therapy for indications such as lipid disorders, skin disorders (e.g. psoriasis), diabetes, cancer, and obesity. For lipid disorders, the FXR modulators of the present invention are used in a combination dose with statins, including, but not limited to, mevastatin, lovastatin, simvastatin, pravastatin, fluvastatin, and atorvastatin calcium; bile acid sequestrants, including, but not limited to, cholestryamine and colestipol; probucol; nicotinic acid; and fibrates including, but not limited to, gemfibrozil and clofibrate.

For skin disorders, the FXR modulators of the present invention are used in a combination dose with corticosteroids; retinoids (such as etretinate); vitamin D analogs (such as calcipotriene); cyclosporine, and antimetabolites (such as aminopterin and methotrexate).

For diabetes, the FXR modulators of the present invention are used in a combination dose with insulin; sulfonylureas including, but not limited to, tolbutamide, acetohexamide, tolazamide, glibenclamide, glyburide, glipizide, and gliclazide; biguanides including, but not limited to, as metformin; and thiazolidinediones including, but not limited to, rosiglitazone, troglitazone, and pioglitazone.

For cancer, the FXR modulators of the present invention are used in a combination dose with antimitotic agents including, but not limited to, paclitaxel, vincristine, etoposide, T138067 (Tularik Inc., South San Francisco Calif.), and T900607 (Tularik Inc., South San Francisco Calif.); alkylating agents including, but not limited to, mechlorethamine, cyclophosphamide, and carmustine; antimetabolites including, but not limited to, methotrexate, gemcitabine, lometrexol, 5-fluorouracil, and 6-mercaptopurine; cytotoxic antibiotics including, but not limited to, doxorubicin, daunorubicin, bleomycin, mitomycin C, and streptozocin; platinum agents including, but not limited to, cisplatin and carboplatin; hormonal agents including, but not limited to, anti-estrogens such as tamoxifen and diethylstilbestrol as well as anti-androgens such as flutamide; anti-angiogenesis agents; and farnesyl transferase inhibitors.

Moreover, for obesity, the FXR modulators of the present invention are used in a combination dose with dexfenfluramine, phenylpropanolamine, orlistat, and sibutramine.

EXAMPLES

Materials and Methods

Reagents and solvents used below can be obtained from commercial sources such as Aldrich Chemical Co. (Milwaukee, Wis., USA). ¹H-NMR spectra were recorded on a Varian Gemini 400 MHz NMR spectrometer. Significant peaks are tabulated in the order: number of protons, multiplicity (s, singlet; d, doublet; t, triplet; q, quartet; m, multiplet; br s, broad singlet) and coupling constant(s) in Hertz (Hz). Electron Ionization (EI) mass spectra were recorded on a Hewlett Packard 5989A mass spectrometer. Mass spectrometry results are reported as the ratio of mass over charge, followed by the relative abundance of each ion (in parentheses). In tables, a single m/e value is reported for the M+H (or as noted M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM NH₄OAc in acetonitrile/water as delivery solvent.

Example 1

This example illustrates the preparation of compound 1.1.4 in FIG. 1A as a representative example of compounds of Formula I. Generally, the compounds of Formula I can be prepared by standard amide couplings known to those in the art.

Synthesis of compound 1.1.4:

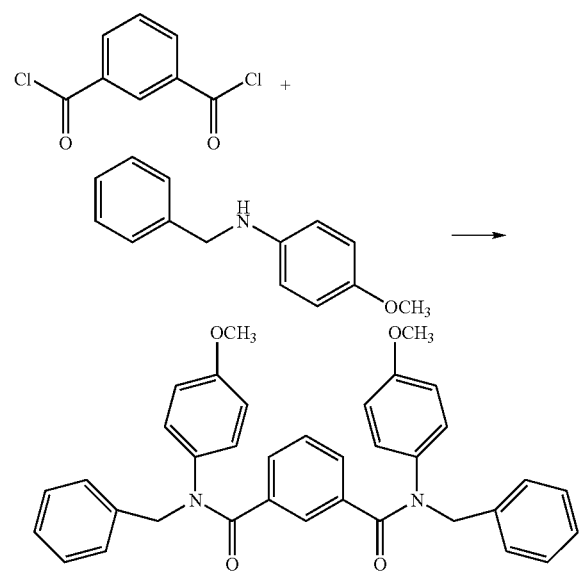

1.1.4

To a mixture of isophthaloyl dichloride (0.457 g) in methylene chloride was added N-benzyl-p-anisidine (0.85 g), followed by pyridine (330 µL). The reaction was stirred at room temperature and the reaction progress was monitored by TLC. Upon completion, PS-Trisamine resin (0.74 g, loading 4.06 mmol/g, Argonaut) was added and stirred for 1 hour. The solution was filtered and the solvent was removed under vacuum. The resulting solid was recrystallized from hexane and ethyl acetate to provide the title compound as white crystals (1.25 g, mp 131° C.). ¹H NMR (400 MHz) (DMSO) δ 7.30 (m, 5H); 7.23 (m, 6H); 7.10 (m, 3H), 6.70 (m, 8H), 4.99 (s, 4H), 3.60 (s, 6H) MS ESI m/e: 557 (M+H).

Example 2

Figure 1C:
Figure 1C:
Figure 1C:
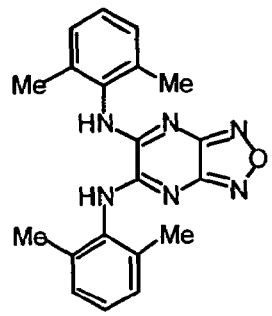
Figure 1C:
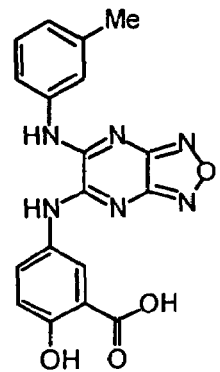
Figure 1C:
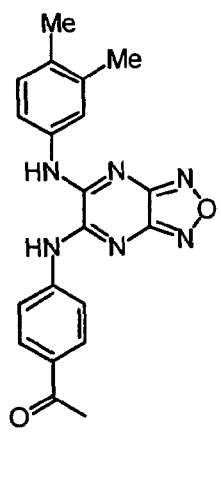
Figure 1C:
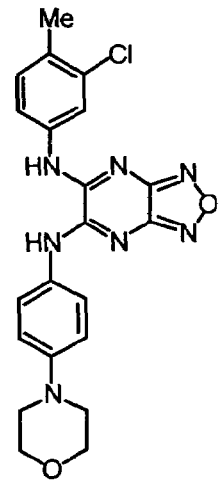
Figure 1C:
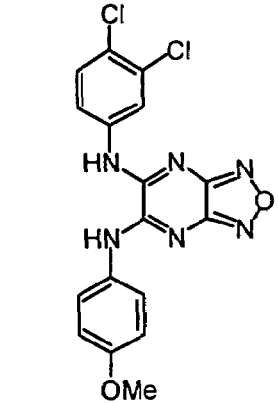
Figure 1C:
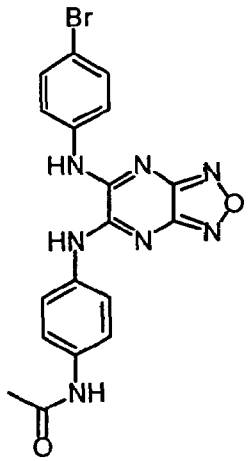
Figure 1C:
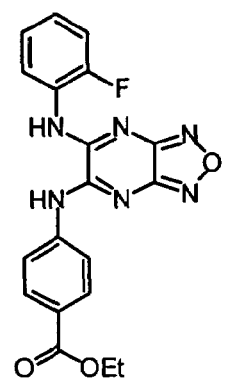
Figure 1C:
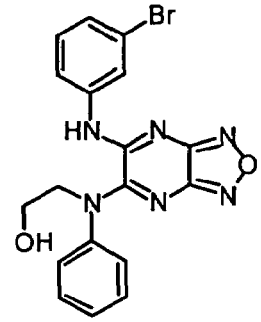
Figure 1C:
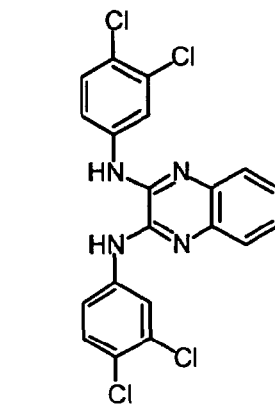
Figure 1C:
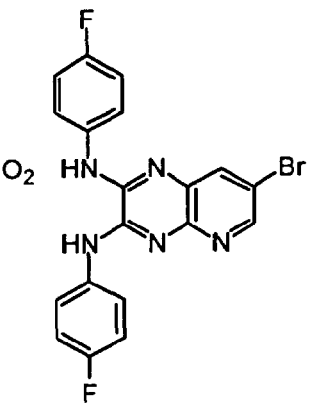
Figure 1D:
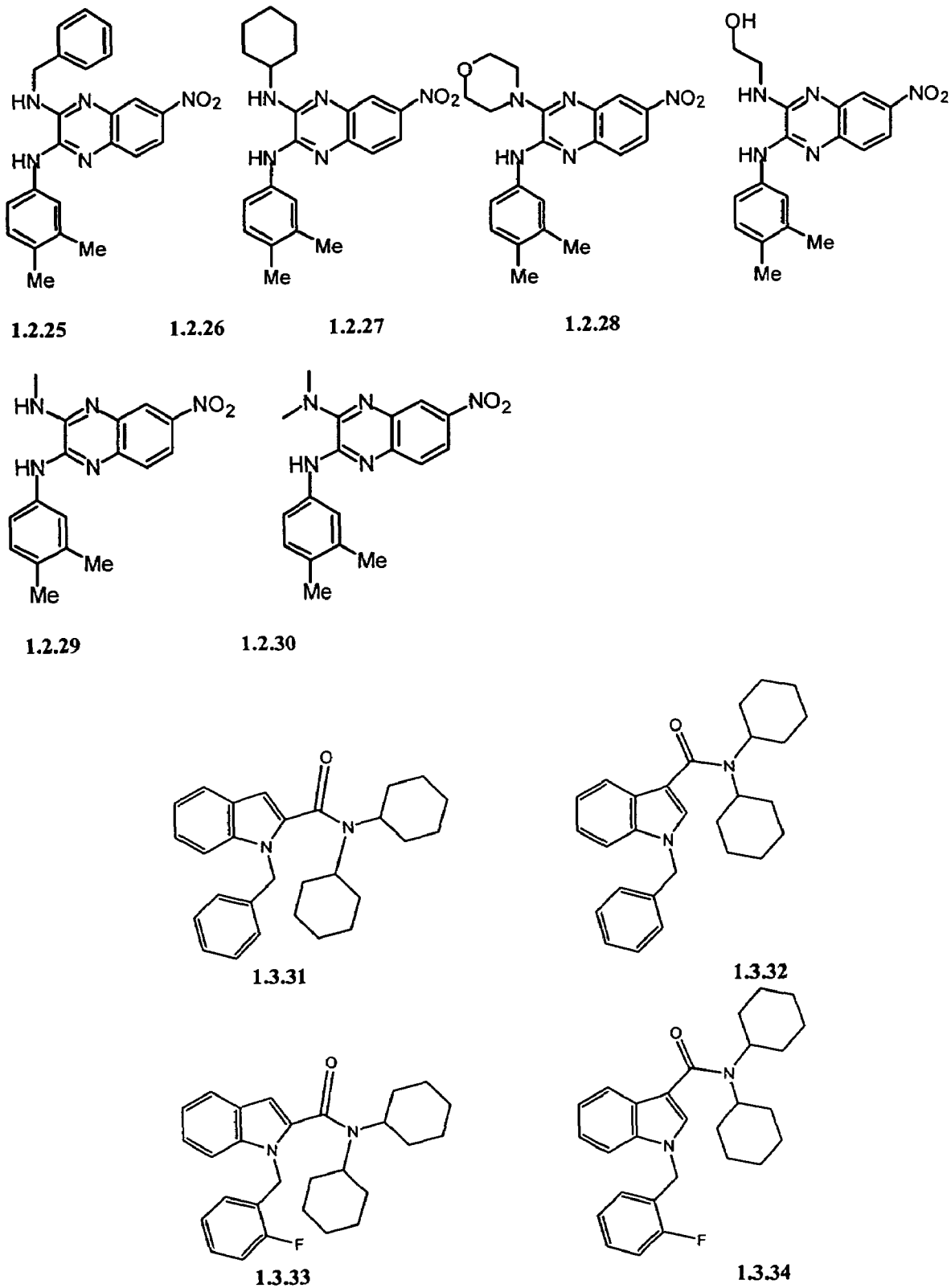
Figure 1E:
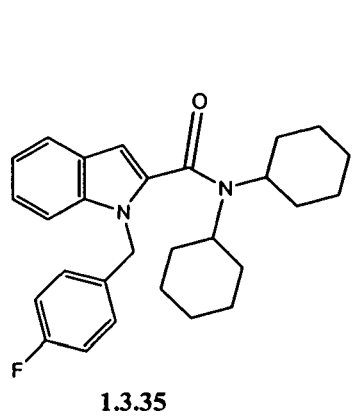
Figure 1E:
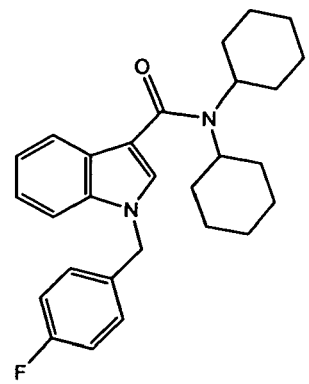
Figure 1E:
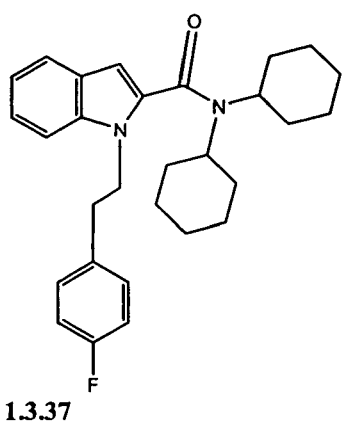
Figure 1E:
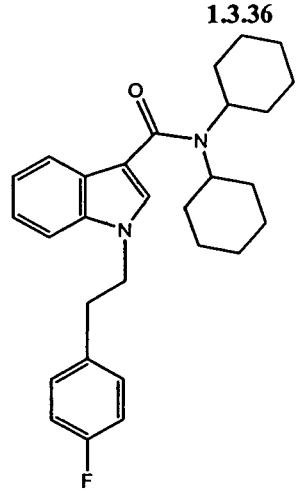

This example illustrates the preparation of compound 1.2.23 in FIG. 1C as a representative example of compounds of Formula I. In certain instances, the compounds of Formula I can be prepared by standard nucleophilic aromatic substitution reactions ($S_NAr$) known to those in the art.

Synthesis of compound 1.2.23:

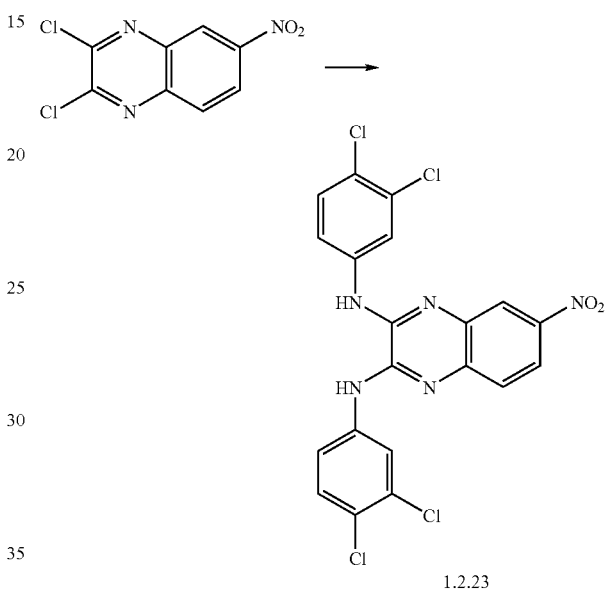

1.2.23

A 10 mL round-bottomed flask was charged with 2,3-dichloro-6-nitroquinoxaline (350 mg, 1.47 mmol, prepared according to the method of Hinsberg and Pollak: Ber. 1896, 29, 784), 3,4-dichloroaniline (710 mg, 4.41 mmol), triethylamine (1.0 mL, 7.35 mmol), and 1.0 mL of anhydrous DMF. This mixture was heated to 150° C. for 72 hours. The reaction was then cooled and poured over ice-water. The organics were extracted into EtOAc, dried over MgSO₄, and concentrated to an orange oil. This oil was purified by flash chromatography (1:1 CH₂Cl₂:hexanes). The desired fractions were combined, concentrated, and the residue recrystallized from hot EtOAc/hexanes to yield 45 mg of a bright orange solid. An analytical sample was recrystallized a second time from hot EtOAc/hexanes (m. p. >300° C.). ¹H NMR (400 MHz) (d₆-DMSO) δ 9.66 (s, 1H); 9.53 (s, 1H); 8.36 (d, J=1.9 Hz, 1H); 8.29 s, 1H); 8.24 (d, J=1.2 Hz, 1H); 8.17 (dd, J=9.1, 2.2 Hz, 1H); 7.94 (dd, J=9.0, 1.8 Hz, 1H); 7.73-7.66 (m, 3H) MS ESI m/e: 492.0 (M−H).

Example 3

This example illustrates the synthesis of compound 1.2.26:

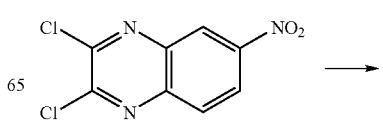

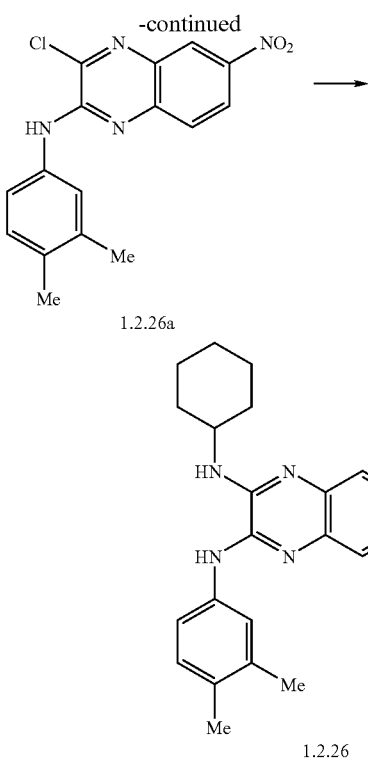

1.2.26a 1.2.26

Preparation of Compound 1.2.26a.

A 100 mL round-bottomed flask was charged with 2,3-dichloro-5-nitroquinoxaline (7.77g, 31.8 mmol), 3,4-dimethylaniline (7.71 g, 63.6 mmol), triethylamine (22 mL, 159.0 mmol), and anhydrous DMF (20 mL). This was heated at 50° C. overnight. The flask was cooled to room temperature, and the contents were poured over 300 mL of ice-water. This was extracted with 2×200 mL of EtOAc. The organics were combined and washed with 100 mL 1N HCl, 100 mL $H_2O$, and 50 mL brine; dried over $Na_2SO_4$, and concentrated to an orange oily solid in vacuo. The product was further purified using flash chromatography ($SiO_2$ gel, 10% EtOAc/hexanes). The desired fractions were concentrated to yield a yellow solid, which was recrystallized, from hot EtOAc/hexanes to yield compound 1.2.30 as yellow crystals (7.12 g, mp 162° C.). $^1H$ NMR (400 MHz) ($d_6$-DMSO) δ 9.49 (1H, s); 8.60 (1H, d, J=2.6 Hz); 8.35 (1H, dd, J=9.2, 2.6 Hz); 7.77 (1H, d, J=9.2 Hz); 7.59 (2H, m); 7.17 (1H, d, J=8.8 Hz); 2.26 (3H, s); 2.23 (3H, s). MS ESI m/e: 327.1 (M−H).

Conversion of 1.2.26a to 1.2.26.

A 10 mL pressure tube was charged with compound 1.2.30 (200 mg, 0.61 mmol), cyclohexylamine (180 mg, 1.82 mmol), triethylamine (308 mg, 3.04 mmol), and anhydrous DMF (0.5 mL). The tube was sealed and heated at 50° C. for 1.5 hours. The reaction was cooled to room temperature and poured over 30 mL of ice-water. This was extracted with 2×50 mL of EtOAc. The combined organics were dried over $Na_2SO_4$ and concentrated to a red solid. Recrystallization from hot EtOAc gave compound 26 as fine orange crystals (191 mg, mp 223° C.). $^1H$ NMR (400 MHz) ($d_6$-DMSO) δ 9.12 (1H, s); 8.16 (1H, d, J=2.6 Hz); 7.98 (1H, dd, J=8.9, 2.6 Hz); 7.65 (1H, dd, J=8.1, 2.2 Hz); 7.57 (1H, d, J=1.8 Hz); 7.53 (1H, d, J=8.9 Hz); 7.36 (1H, d, J=6.9 Hz); 7.17 (1H, d, J=8.2 Hz); 4.20-4.09 (1H, m); 2.27 (3H, s); 2.23 (3H, s); 2.11-2.08 (2H, m); 1.83-1.79 (2H, m); 1.70-1.66 (1H, m); 1.45-1.25 (5H, m). MS ESI m/e: 398.1 (M−H).

Example 4

Figure 2A:
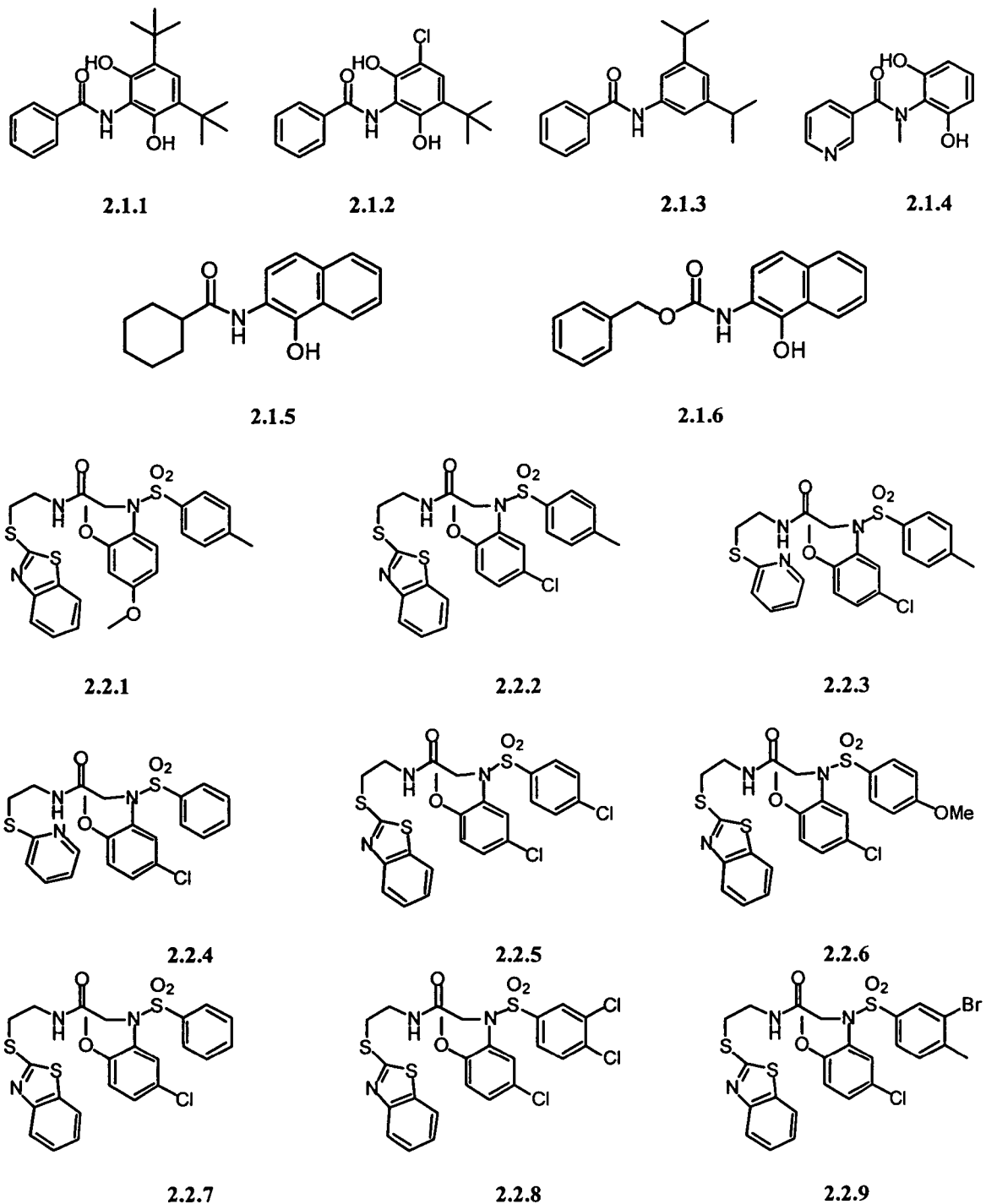
FIGS. 2(A-B) provide structures of compounds of Formula II.

This example illustrates the preparation of compound 2.1.1 in FIG. 2A as a representative example of compounds of Formula II. Generally, the compounds of Formula II can be prepared by standard methods known to those in the art.

Synthesis of compound 2.1.1:

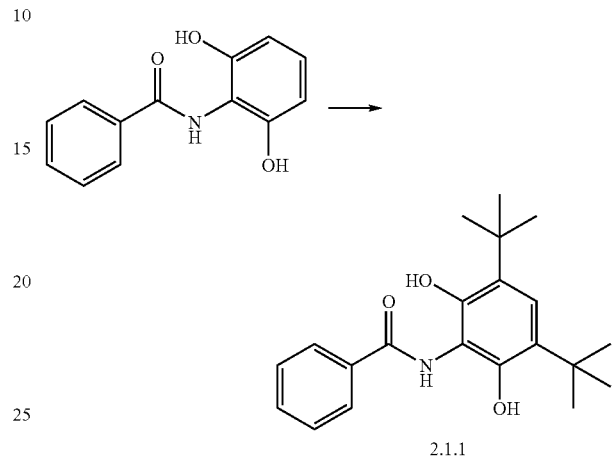

2.1.1

N-(2,6-dihydoxy-phenyl)-benzamide (7 g, 30.5 mmol, described in Chem. Ber. 1958, 91, 1123-1125) was suspended in 85% $H_3PO_4$ (150 mL) and 2-methyl-2-propanol (95 mL, 68.4 g, 922 mmol). The reaction mixture was vigorously stirred for 16 hours and then poured into 500 mL of deionized water and extracted with 500 mL of EtOAc. The aqueous layer was carefully treated with 50 g of $NaHCO_3$ to partially neutralize the phosphoric acid and aid in layer separation. The aqueous layer was again extracted with 200 mL of EtOAc. The combined organic layers were washed 1×100 mL sat. brine, dried over $Na_2SO_4$, filtered, and concentrated to a tan amorphous solid. Trituration with $CH_2Cl_2$/hexanes resulted in the formation of a fine white solid, which was collected by filtration, rinsed with hexanes, and dried under vacuum. The product (8.9 g, 85% yield, mp 197° C.) was found to be >95% pure by HPLC. $^1H$ NMR (400 MHz) ($CD_3CN$) δ 8.49 (bs, 1H); 8.05 (d, J=7.2 Hz, 2H); 7.64 (t, J=6.5 Hz, 1H); 7.57 (t, J=7.0 Hz, 2H); 7.18 (s, 1H); 6.91 (s, 2H); 1.39 (s, 18H). MS ESI m/e: 342.2 (M+H), 364.1 (M+Na)

Example 5

Figure 2B:
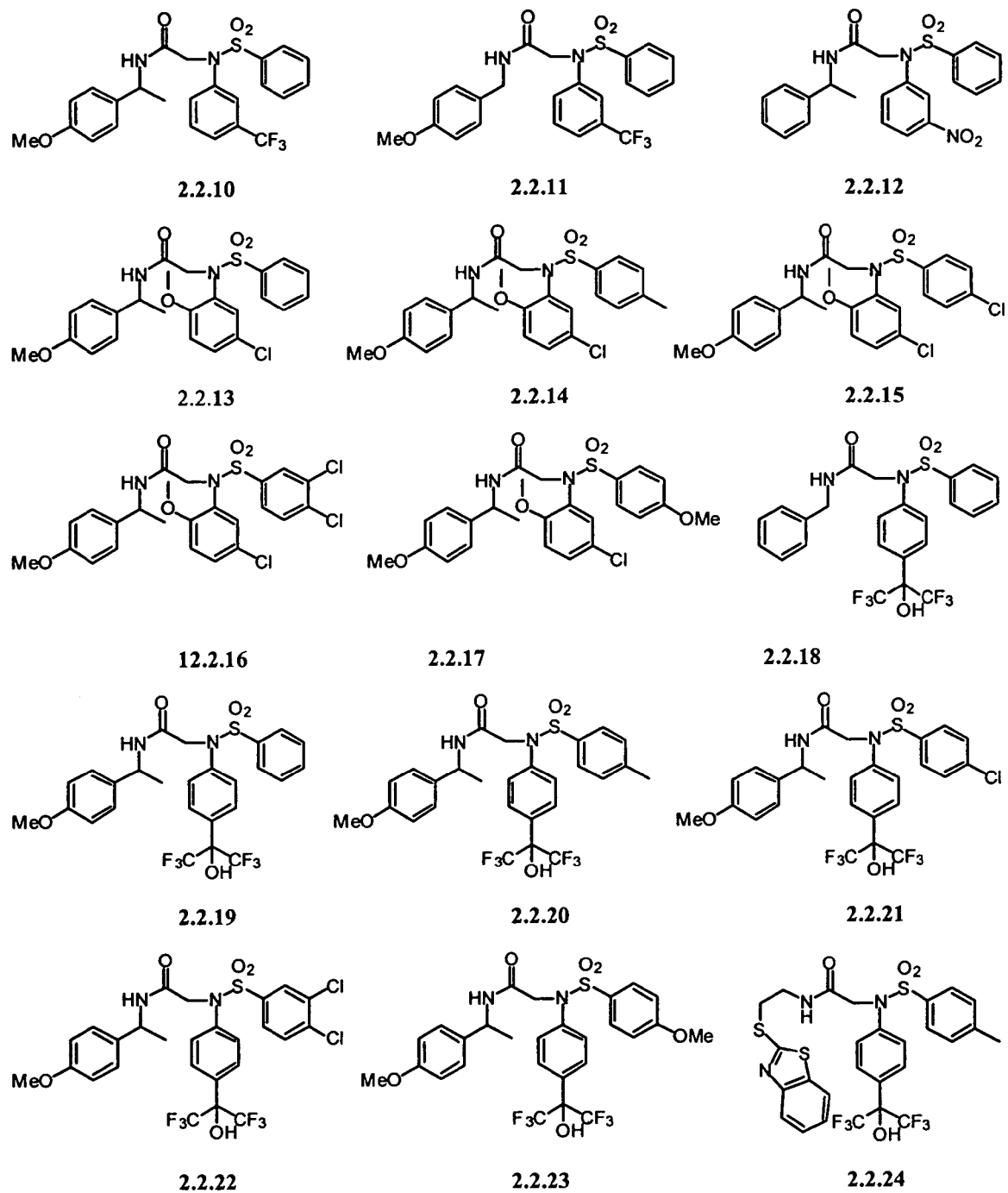

This example illustrates the synthesis of compound 2.2.10 in FIG. 2B:

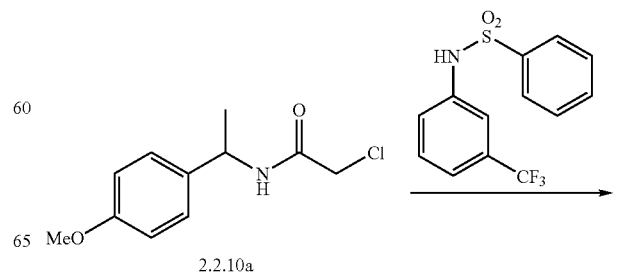

2.2.10a

-continued

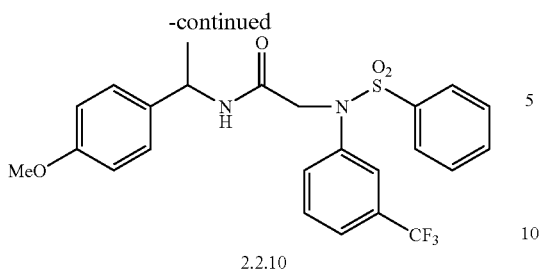

2.2.10

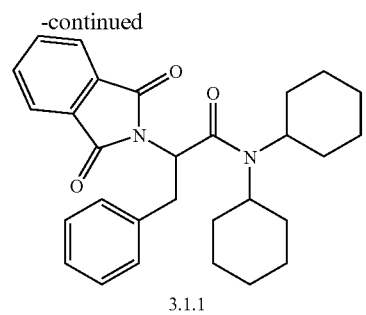

3.1.1

N-(3-trifluoromethyl-phenyl)-benzenesulfonamide (2 g, 6.6 mmol, described in *Coll. Chech. Chem. Comm.* 1987, 52, 2900-2908.) was dissolved in anhydrous THF (6 mL) and then treated with potassium tert-butoxide (6.5 mL of 1.0 N solution in THF). After five min., chloroacetamide 2.2.10a (1.4 g, 6.2 mmol, described in *J. Ind. Chem. Soc.* 1963, 40, 885-888.) was added in one portion and Bu$_4$NI (229 mg, 0.62 mmol) was added to catalyze the alkylation. The reaction mixture was warmed to 50° C. After 16 h, the reaction was complete by TLC analysis. The reaction mixture was poured into sat. NH$_4$Cl$_{(aq)}$ and diluted with 1:1 ethyl acetate/hexanes. The aqueous phase was extracted 1×50 mL ethyl acetate and the combined organic layers were washed with sat. brine, dried over Na$_2$SO$_4$, filtered, and concentrated to a light yellow oil. Purification by flash chromatography (silica gel, eluting with 40% ethyl acetate/hexanes) afforded an amorphous solid, which could be crystallized only from ether/hexanes at −20° C. After filtration, rinsing with hexanes, and drying under vacuum, compound 2.2.10 was obtained as a fine white powder (2.1 g, m. p. 93° C.). $^1$H NMR (400 MHz) (CDCl$_3$) δ 7.64 (t, J=7.6 Hz, 1H); 7.62-7.46 (m, 5H); 7.41 (t, J=8.0 Hz, 1H); 7.29 (s, 1H); 7.20 (d, J=8.0 Hz, 1H); 7.10 (d, J=8.8 Hz, 2H); 6.82 (d, J=8.4 Hz, 2H); 6.60 (d, J=8.4 Hz, 1H); 5.00 (quintet, J=7.2 Hz, 1H); 4.28 (d, J=16.8 Hz, 1H); 4.12 (d, J=16.8 Hz, 1H); 3.79 (s, 3H); 1.44 (d, J=6.8 Hz, 3H). MS ESI m/e: 493.1 (M+H), 515.2 (M+Na).

Example 6

Figure 3A:
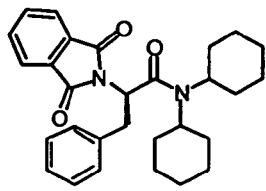
FIGS. 3(A-D) provide structures of compounds of Formula III.
Figure 3A:
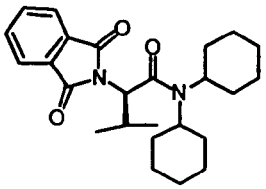
Figure 3A:
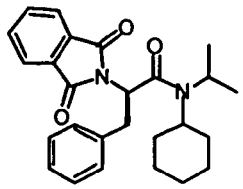
Figure 3A:
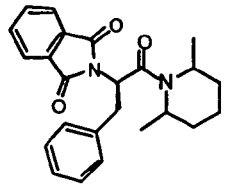
Figure 3A:
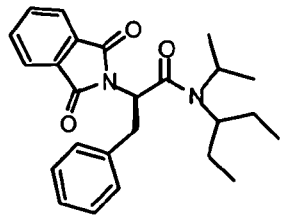
Figure 3A:
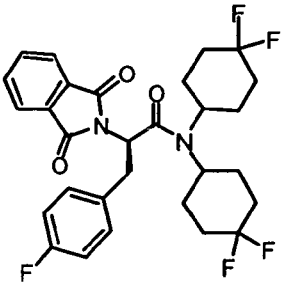
Figure 3A:
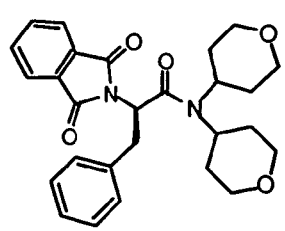
Figure 3A:
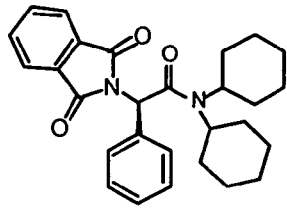
Figure 3A:
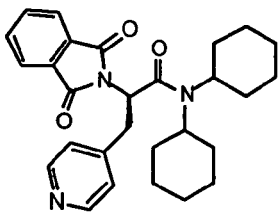
Figure 3A:
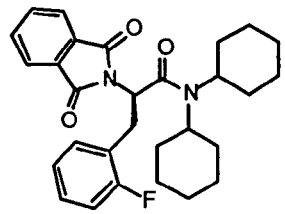
Figure 3A:
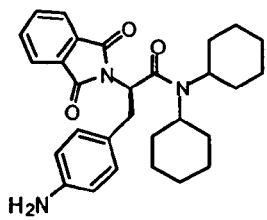
Figure 3A:
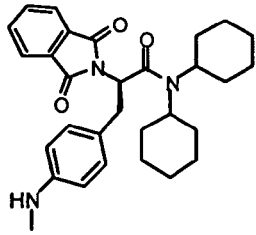
Figure 3A:
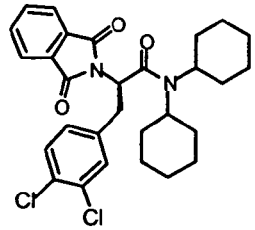
Figure 3A:
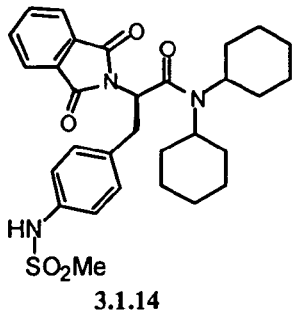
Figure 3A:
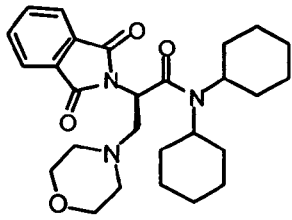
Figure 3A:
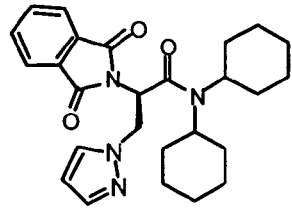
Figure 3B:
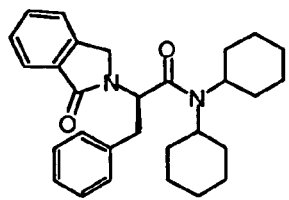
Figure 3B:
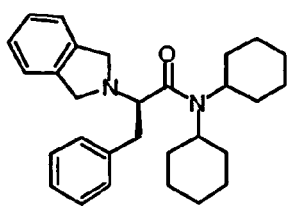
Figure 3B:
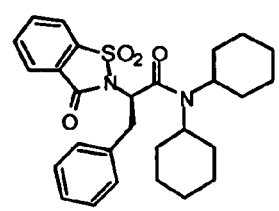
Figure 3B:
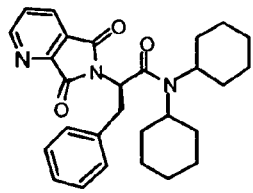
Figure 3B:
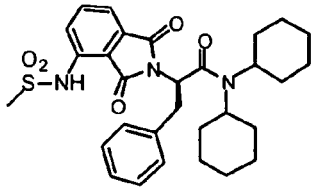
Figure 3B:
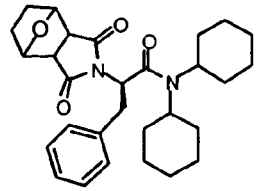
Figure 3B:
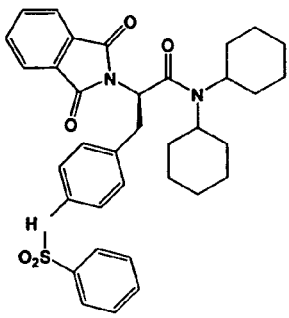
Figure 3B:
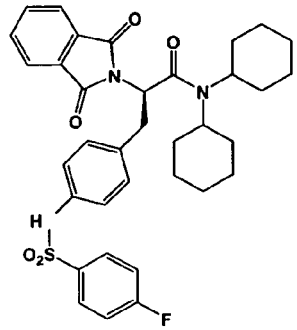
Figure 3B:
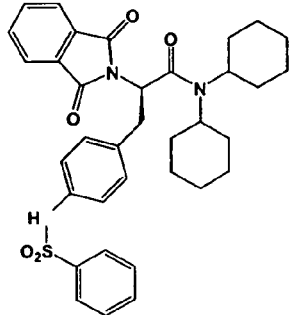
Figure 3B:
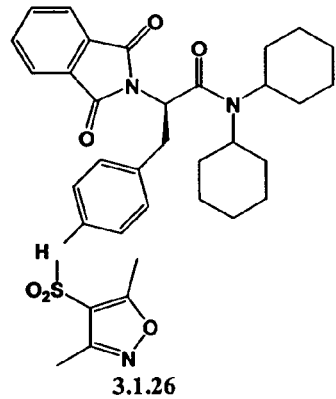
Figure 3B:
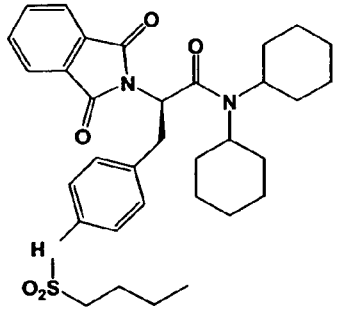
Figure 3B:
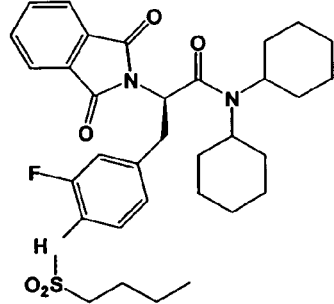
Figure 3B:
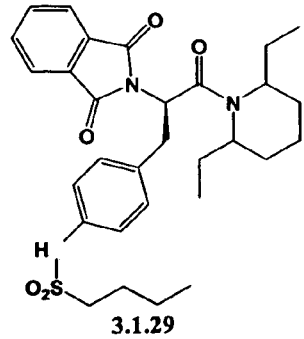
Figure 3B:
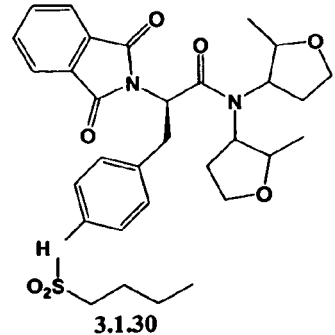
Figure 3B:
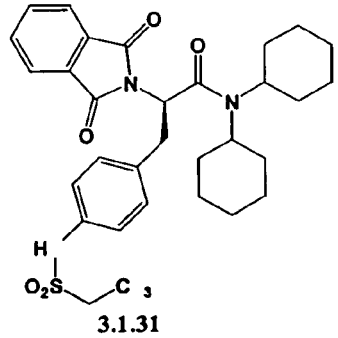

This example illustrates the preparation of compound 3.1.1 in FIG. 3A as a representative example of compounds of Formula III. Generally, the compounds of Formula III can be prepared by standard amide couplings known to those in the art.

Synthesis of compound 3.1.1:

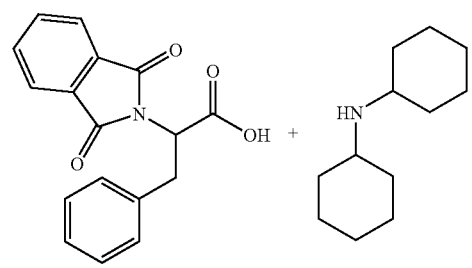

N-phthaloyl-DL-phenylalanine (8.23 g, 0.028 mol, described in *J. Am. Chem. Soc.* 1948, 70, 1473) was treated with POCl$_3$ (25 ml, 0.27 mol) and the resultant mixture heated at 75° C. for 3 hours, during which time the reaction mixture became a yellow solution. Excess POCl$_3$ was removed (by rotary evaporation followed by high vacuum pump for 1 hour) and the residue dissolved in dichloromethane (100 ml) and treated with dicyclohexylamine (8.5 ml, 0.04 mol). The reaction mixture was stirred at room temperature for 4 hours before being filtered; the solvent was evaporated and the crude product purified by flash column chromatography (eluant: 50% ethyl acetate in hexanes) to afford the title compound as a white solid (7.08 g, mp 183° C.).

$^1$H NMR (400 MHz) (CDCl$_3$): δ 7.78 (m, 2H); 7.70 (m, 2H); 7.19 (m, 5H); 5.26 (m, 1H); 3.65 (m, 1H); 3.41 (m, 1H); 2.88 (m, 1H); 2.57 (m, 2H); 1.34 (m, 19H) ppm. MS ESI m/e: 459.2 (M+H).

Example 7

Figure 3C:
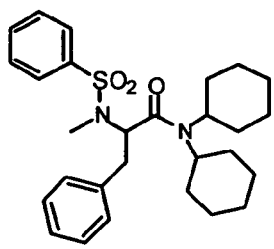
Figure 3C:
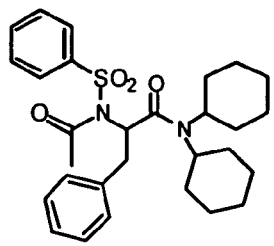
Figure 3C:
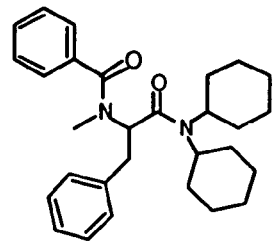
Figure 3C:
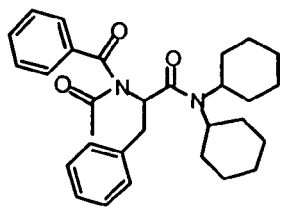
Figure 3C:
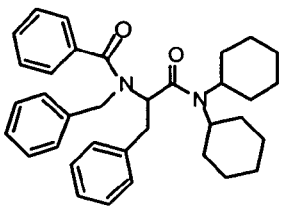
Figure 3C:
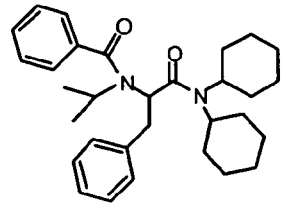
Figure 3C:
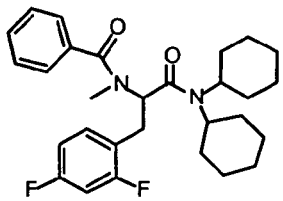
Figure 3C:
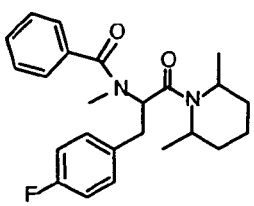
Figure 3C:
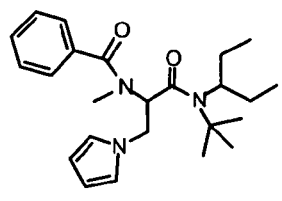
Figure 3C:
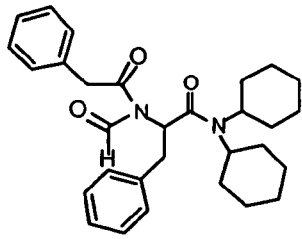
Figure 3C:
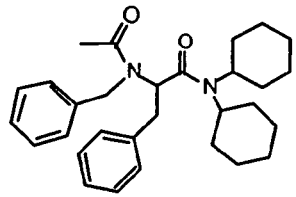
Figure 3C:
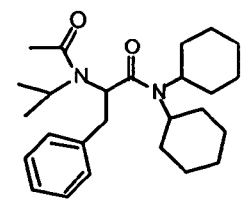
Figure 3C:
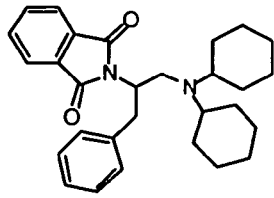
Figure 3C:
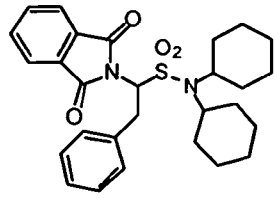
Figure 3C:
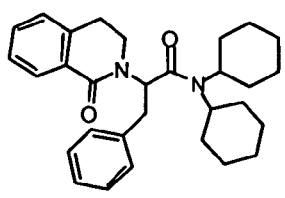
Figure 3D:
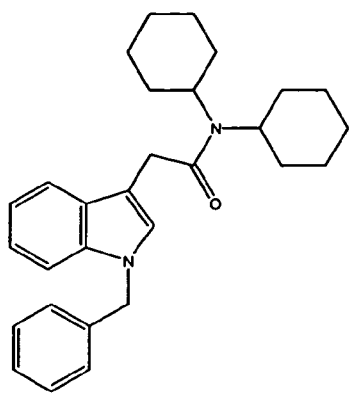
Figure 3D:
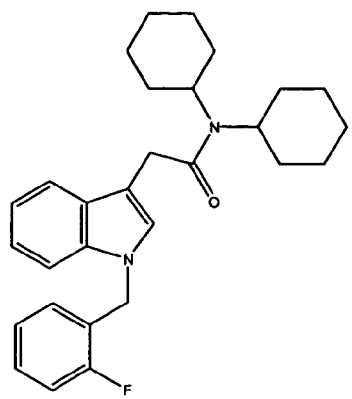
Figure 3D:
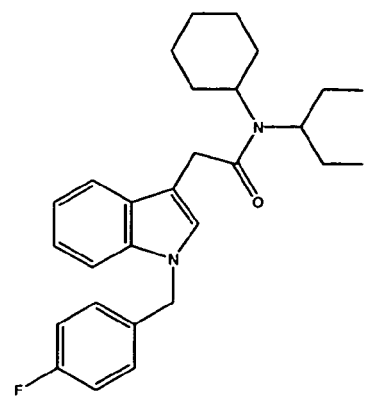
Figure 3D:
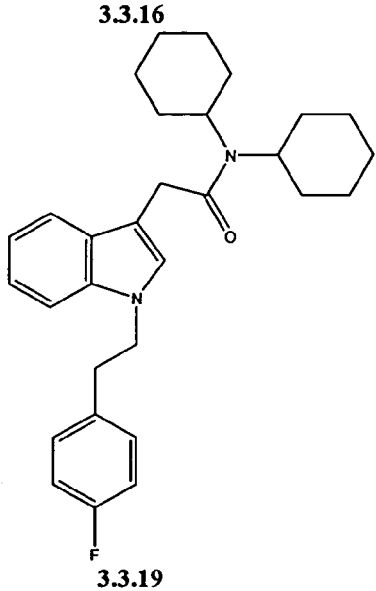
Figure 3D:
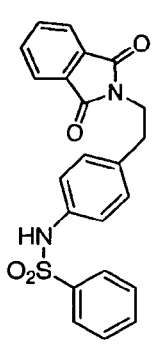
Figure 3D:
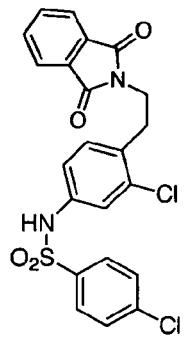
Figure 3D:
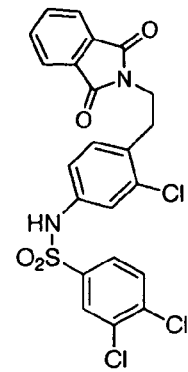
Figure 3D:
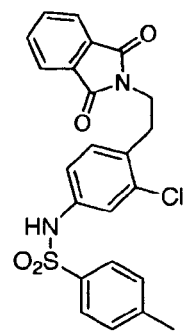
Figure 3D:
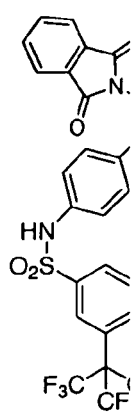

This example illustrates the preparation of compound 3.2.3 in FIG. 3C as a representative example of compounds of Formula III. Generally, the compounds of Formula IV can be prepared by standard amide couplings known to those in the art.

Synthesis of compound 3.2.3:

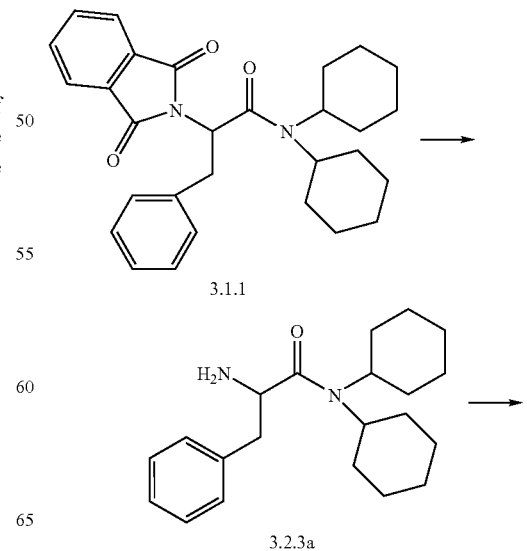

-continued

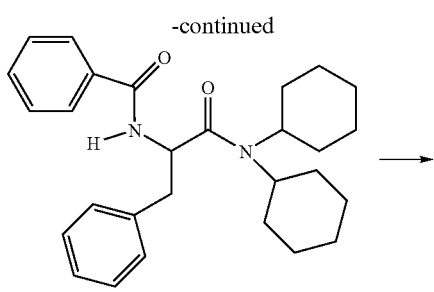

3.2.3b

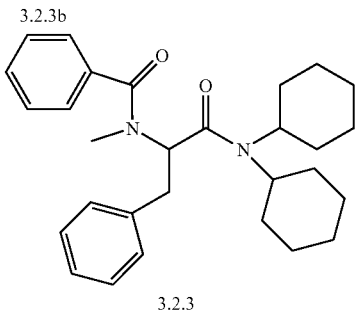

3.2.3

Conversion of 3.1.1 to 3.2.3a.

To a solution of the phthalimide substrate A (5.70 g, 0.012 mol) in 2-propanol (75 ml) and water (10.5 ml) was added NaBH$_4$ (2.33 g, 0.06 mol) and the reaction mixture stirred at room temperature overnight. Acetic acid (12.5 ml) was added dropwise, the reaction flask was stoppered and the mixture heated to 80° C. for 4 hours. The reaction mixture was cooled to room temperature, poured into water and neutralised with solid sodium bicarbonate. The aqueous mixture was extracted with ethyl acetate, the combined organic phase dried and the solvent evaporated. The product was used without further purification. MS ESI m/e: 329.3 (M+H).

Conversion of 3.2.3a to 3.2.3b.

To a solution of crude 3.2.3a (203 mg, 0.62 mmol) in dichloromethane (5 ml) at 0° C. was added triethylamine (0.1 ml, 0.72 mmol) followed by benzoyl chloride (0.085 ml, 0.73 mmol) and the reaction mixture allowed to warm to room temperature and stirred for 3 hours. The reaction was quenched by the addition of 0.05 M NaOH (aq) and the aqueous layer extracted with dichloromethane. The combined organic phase was dried (Na$_2$SO$_4$), the solvent evaporated and the crude product purified by flash column chromatography (eluant: 20% ethyl acetate in hexanes). MS ESI m/e: 433.3 (M+H), 455.3 (M+Na).

Conversion of 3.2.3b to 3.2.3.

To 3.2.3b (62 mg, 0.14 mmol) in a 1:1 mixture of THF and DMF (20 ml) at 0° C. was added sodium hydride (8 mg, 0.20 mmol of a 60% dispersion in mineral oil) and the resultant mixture stirred at 0° C. for 20 minutes before being allowed to warm to room temperature. Iodomethane (0.014 ml, 0.22 mmol) was then added to the reaction mixture and the resultant mixture stirred at room temperature for 4 h. Water was added to quench the reaction and the aqueous layer was extracted with ethyl acetate. The combined organic phase was dried (MgSO$_4$), the solvent evaporated in vacuo and the crude product purified by flash column chromatography (eluant: 20% ethyl acetate in hexanes) to afford compound 3.2.3 as a white solid (58 mg, mp 123.1° C.). $^1$H NMR (400 MHz) (CDCl$_3$): δ 7.29 (m, 8H); 6.99 (m, 2H); 5.94 (t, J=8.0 Hz, 1H); 3.89 (m, 1H); 3.33 (m, 1H); 3.12 (m, 1H); 2.95 (m, 1H); 2.85 (s, 3H); 2.52 (m, 2H); 1.42 (m, 18H). MS ESI m/e: 447.4 (M+H).

Example 8

Figure 4A:
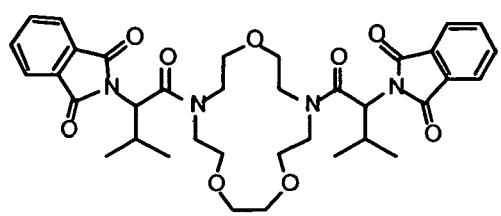
FIGS. 4(A-C) provide structures of compounds of Formula IV.
Figure 4A:
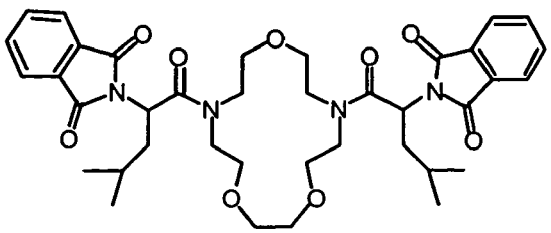
Figure 4A:
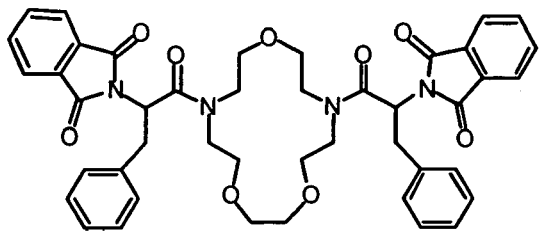
Figure 4A:
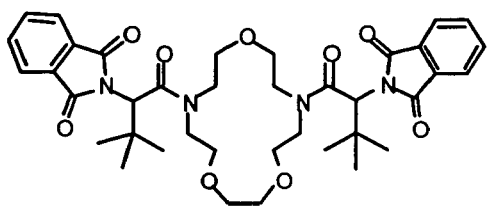
Figure 4A:
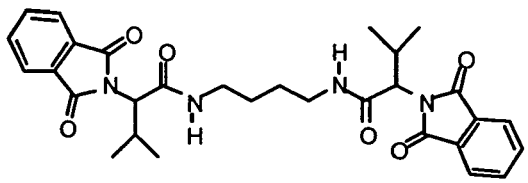
Figure 4A:
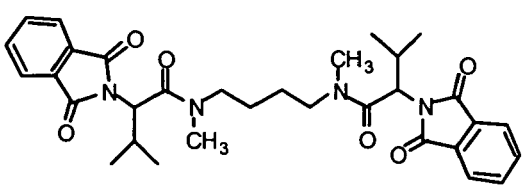
Figure 4A:
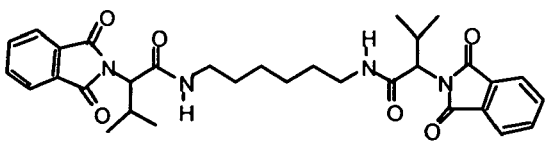
Figure 4A:
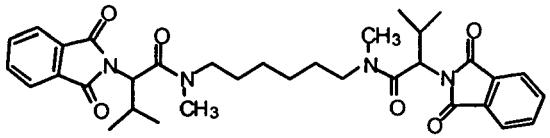
Figure 4A:
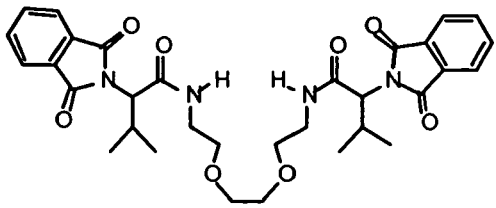
Figure 4A:
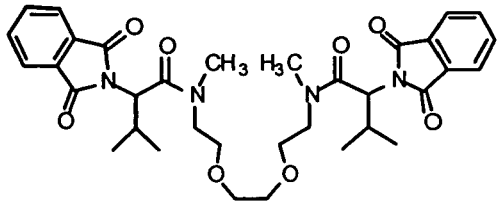
Figure 4B:
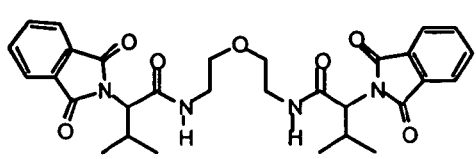
Figure 4B:
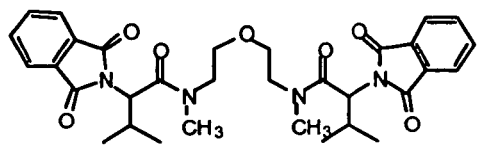
Figure 4B:
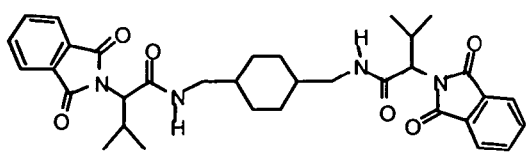
Figure 4B:
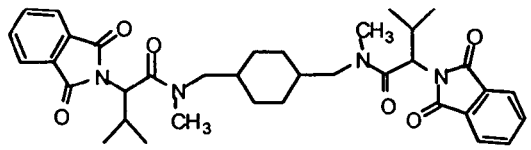
Figure 4B:
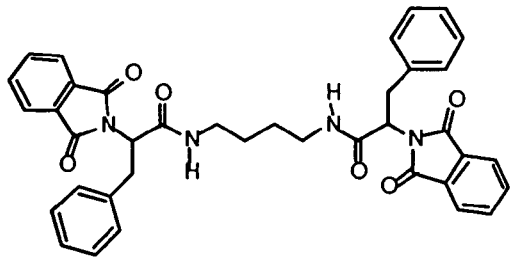
Figure 4B:
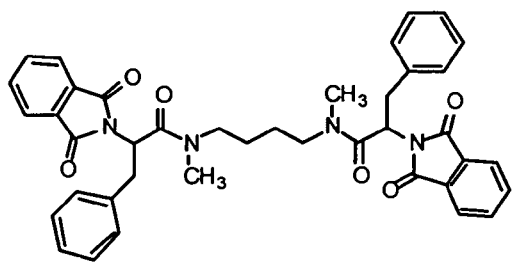
Figure 4B:
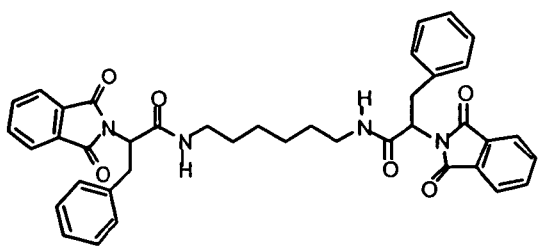
Figure 4B:
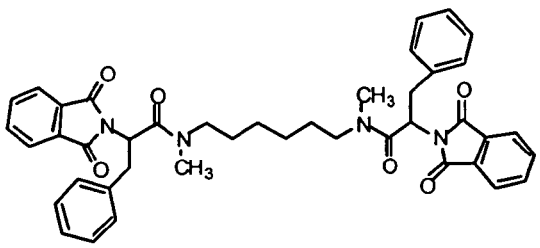
Figure 4B:
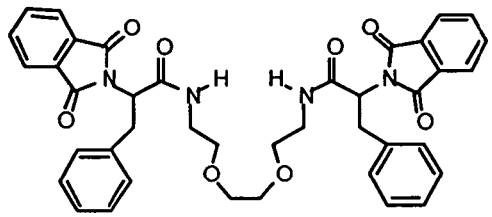
Figure 4B:
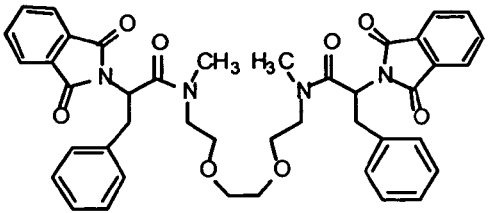
Figure 4C:
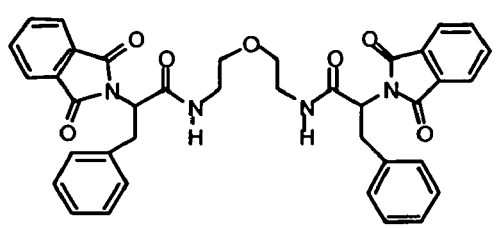
Figure 4C:
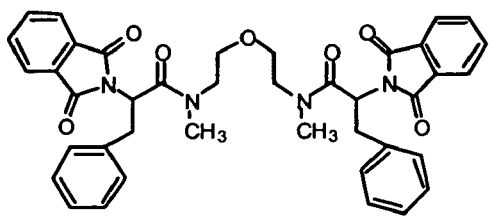
Figure 4C:
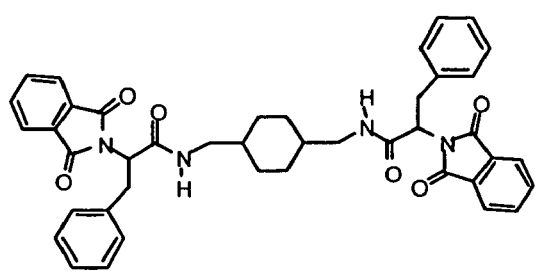
Figure 4C:
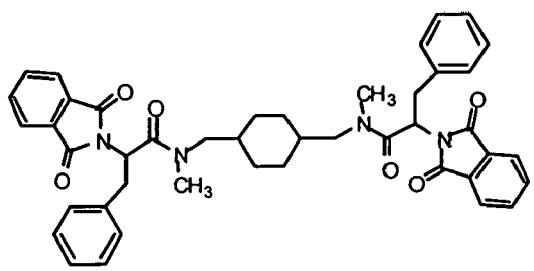
Figure 4C:
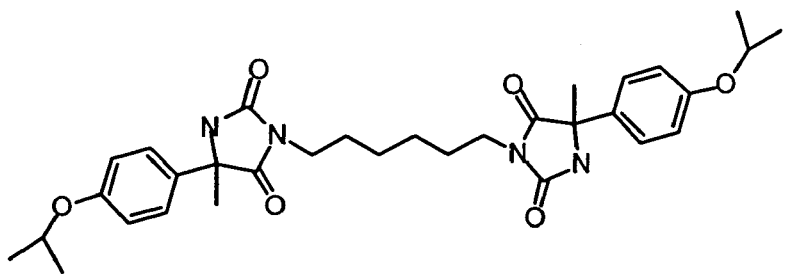

This example illustrates the preparation of compound 4.7 in FIG. 4A as a representative example of compounds of Formula IV. Generally, the compounds of Formula V can be prepared by standard amide couplings known to those in the art.

Synthesis of compound 4.7:

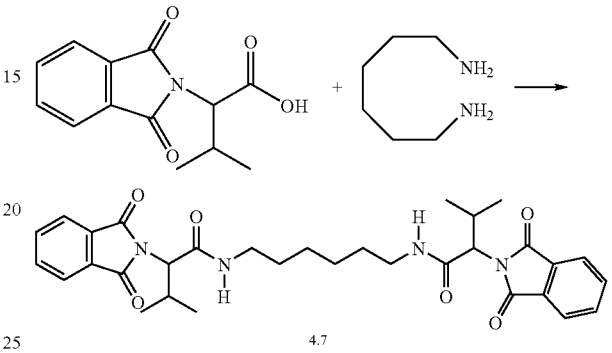

4.7

To a solution of N-phthaloyl-DL-valine (306 mg, 1.24 mmol, described in J. Am. Chem. Soc. 1948, 70, 1473) in DMF (10 mL) was added 1-hydroxy-7-azabenzotriazole (166 mg, 1.22 mmol) and 1,6-hexanediamine (76 mg, 0.65 mmol), followed by O-(7-azabenzotriazol-1-yl)-N,N, N',N'-tetramethyluronium hexafluorophosphate (461 mg, 1.21 mmol) and N-methylmorpholine (0.27 mL, 2.46 mmol) and the reaction mixture stirred at room temperature for 3 hours. The reaction mixture was diluted with CH$_2$Cl$_2$ (10 mL) and added to water (100 mL); the aqueous layer was extracted with CH$_2$Cl$_2$ and the combined organic phase evaporated. The crude product was dried (MgSO$_4$) and purified by flash column chromatography (eluant: 50% ethyl acetate in hexanes) to afford the title compound as a white solid (84 mg, mp 165s° C.). $^1$H NMR (400 MHz) (CDCl$_3$): δ 7.88 (m, 4H); 7.73 (m, 4H); 7.04 (br, s, 2H); 4.39 (m, 2H); 3.28 (m, 4H); 2.79 (m, 2H); 1.38 (m, 8H); 1.09 (m, 6H); 0.85 (m, 6H) ppm. MS ESI m/e: 547.2 (M+H).

Example 9

Figure 5:
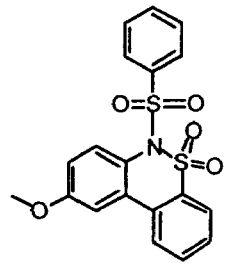
FIG. 5 provides structures of compounds of Formula V.
Figure 5:
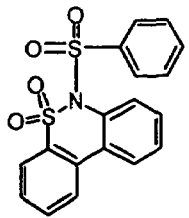
Figure 5:
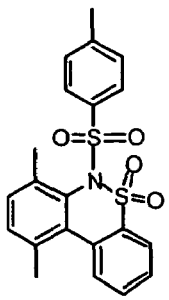
Figure 5:
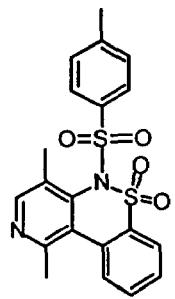
Figure 5:
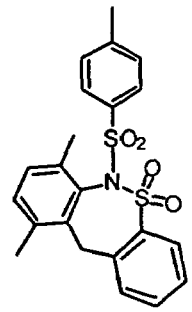
Figure 5:
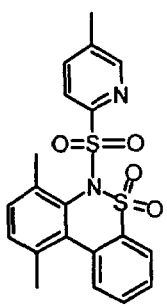
Figure 5:
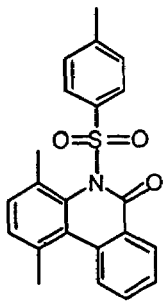
Figure 5:
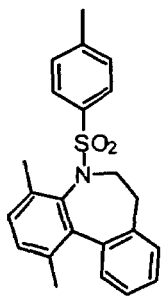

This example illustrates the preparation of compound 5.3 in FIG. 5 as a representative example of compounds of Formula V. Generally, the compounds of Formula V can be prepared by standard methods known to those in the art.

Synthesis of compound 5.3:

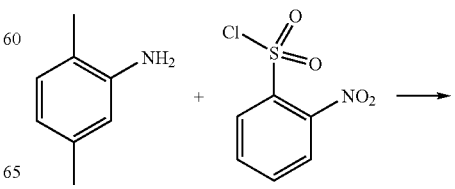

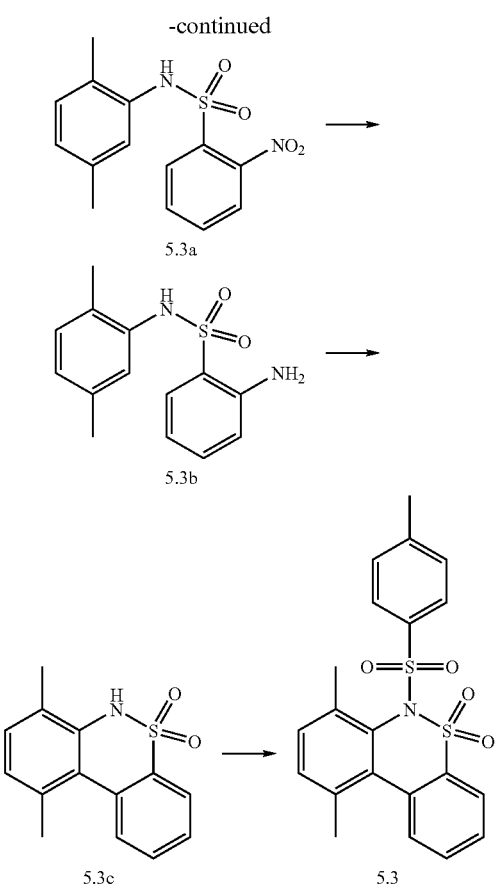

Preparation of sulfonamide 5.3a.

2,5-dimethyl-aniline (2.4 g, 20 mmol) and 2-nitrobenzenesulfonyl chloride (4.4 g, 20 mmol) are dissolved in $CH_2Cl_2$ and treated with pyridine (1.8 mL, 22 mmol). The reaction mixture is stirred at room temperature until TLC shows no starting material. The reaction mixture is quenched with dilute HCl, and the organic layer washed with saturated brine. Drying over $MgSO_4$, filtration, and concentration provides a solid that is recrystallized from hot EtOAc/hexanes to provide 2-nitro-N-(2,5-dimethyl-phenyl)-benzenesulfonamide.

Conversion of 5.3a to 5.3b.

2-nitro-N-(2,5-dimethyl-phenyl)-benzenesulfonamide (6.1 g, 20 mmol) in EtOAc (60 mL) is treated with $SnCl_2.2H_2O$ (22.5 g, 100 mmol). The reaction mixture is heated to reflux for 30 minutes and then allowed to cool to room temperature. 2 N KOH (250 mL, 500 mmol) is added and the resulting mixture stirred vigorously until all solids dissolve. The aqueous layer is separated and extracted 2×100 mL EtOAc. The combined organic layers are washed with sat. brine, dried over $MgSO_4$, filtered, and concentrated to a solid, which is recrystallized from hot EtOAc/hexanes to provide 2-amino-N-(2,5-dimethyl-phenyl)-benzenesulfonamide.

Conversion of 5.3b to 5.3c.

Conversion of 2-amino-N-(2,5-dimethyl-phenyl)-benzenesulfonamide to 1,4-Dimethyl-10H-9-thia-10-aza-phenanthrene 9,9-dioxide is carried out by diazotization according to the method of Ullmann and Gross (Ber. Dtsch. Chem. Ges. 1910, 43, 2694).

Conversion of 5.3c to 5.3.

1,4-Dimethyl-10H—9-thia-10-aza-phenanthrene 9,9-dioxide (2.6 g, 10 mmol) is dissolved in pyridine (10 mL) and treated with p-toluenesulfonyl chloride (2.8 g, 15 mmol). The reaction mixture stirred at 60° C. until TLC shows disappearance of the starting material. The reaction mixture is allowed to cool and then poured into 100 mL of 3N HCl. The mixture is extracted 2×100 mL EtOAc and the combined organic layers are washed with sat. brine, dried over $MgSO_4$, filtered, and concentrated to a solid, which is recrystallized from hot EtOAc/hexanes to give 1,4-dimethyl-10-(toluene-4-sulfonyl)-10H-9-thia-10-aza-phenanthrene 9,9-dioxide.

Example 10

Compounds of the present invention (illustrated by the examples above and in the figures) were evaluated for FXR binding activity. $IC_{50}$ values were measured, representing the concentration of the compound at which 50% of the activity is inhibited. A substantial number of the compounds exhibited $IC_{50}$ values ranging from less than 1 to about 30 µM or more. In preferred embodiments of the invention, the compounds exhibited $IC_{50}$ values of 10 µM or more. In more preferred embodiments, the compounds exhibited $IC_{50}$ values ranging from 1 µM to about 10 µM. In the most preferred embodiments, the compounds exhibited $IC_{50}$ values of less than 1 µM.

Example 11

This Example describes an in vitro assay that is useful to identify compounds that modulate binding of FXR ligands to the FXR ligand binding domain. The ability of compounds of Formulae I-V to affect the binding of a labeled sensor peptide that is derived from the coactivator SRC-1 to an FXR ligand binding domain was tested.

Fluorescence polarization was used to study the effect of compounds of Formulae I-V on the ability of the FXR LBD to bind a sensor peptide. The assay reagents were as follows:

Sensor: Rhodamine-labeled ILRKLLQE peptide (final conc.=1-5 nM). It is noted that the Rhodamine-labeled peptide comprises, at a minimum, the following sequence LXX-LLXX, wherein X is any amino acid. Additional amino acids can be added to both the N-terminus and the C-terminus of this core peptide. In preferred embodiments, the peptide is 8 amino acids in length and, more preferable, about 11 amino acids in length.

Receptor: Glutathione-S-transferase/FXR ligand binding domain fusion protein (final conc.=100-200 nM).

Buffer: 10 mM HEPES, 10 mM NaCl, 6 mM magnesium chloride, pH 7.6.

Protocol

1. Add 90 microliters of Sensor/Receptor mixture to each well of a 96-well microtiter plate.

2. Add 10 microliters of test compound per well.

3. Shake 5 minutes and within 5 minutes determine the amount of fluorescence polarization by using a Fluorolite FPM-2 Fluorescence Polarization Microtiter System (Dynatech Laboratories, Inc.)

Ten ng/µL of GST-FXR fusion protein was mixed with a rhodamine-labeled peptide comprising LXXLLXX, wherein X is any amino acid, and the panel of bile acids (concentrations as indicated). Fluorescence polarization was read after a room temperature incubation and brief shaking. Change in millipolarization (mP) units is the difference treated and untreated samples. The high change in mP units demonstrates that the labeled peptide binds to GST-FXR in a CDCA-dependent manner.

Using fluorescence resonance energy transfer (FRET) one can study the effect of different compounds of Formula I-V on the ability of FXR to bind the coactivator SRC-1.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound of the formula $$B^1\text{-}L^1\text{-}A^1\text{-}L^2\text{-}B^2 \qquad\qquad I$$

or pharmaceutically acceptable salt thereof, wherein:
- $A^1$ is a member selected from the group consisting of cycloalkylene, cycloalkenylene, arylene, heteroarylene, heterocycloalkylene, and heterocycloalkenylene;
- $L^1$ and $L^2$ are each independently a member selected from the group consisting of —O—, —S—, —N($R^1$)—, —C(O)—, —C(O)N($R^1$)—, —O-alkylene-, —S-alkylene-, —N($R^1$)-alkylene, —C(O)-alkylene, —C(O)N($R^1$)-alkylene, and —C(O)—O-alkylene;
- $B^1$ and $B^2$ are each independently a member selected from the group consisting of cycloalkyl, cycloalkenyl, aryl, heteroaryl, heterocycloalkyl, and heterocycloalkenyl; and
- $R^1$ is a member selected from the group consisting of hydrogen, alkyl, heteroalkyl, cycloalkyl, heterocycloalkyl, cycloalkenyl, heterocycloalkenyl, aryl, heteroaryl, and arylalkyl.

2. The compound of claim 1, wherein
- $A^1$ is a member selected from the group consisting of arylene, and heteroarylene;
- $L^1$ and $L^2$ are each independently a member selected from the group consisting of —C(O)— and —C(O)N($R^1$)—;
- $R^1$ is a member selected from the group consisting of ($C_5$-$C_8$)cycloalkyl, aryl, heteroaryl, and aryl($C_1$-$C_4$)alkyl; and
- $B^1$ and $B^2$ are each independently a member selected from the group consisting of aryl, heteroaryl and ($C_5$-$C_8$) cycloalkyl.

3. The compound of claim 1, wherein
- $A^1$ is a member selected from the group consisting of phenylene, and divalent pyridine;
- $L^1$ and $L^2$ are each independently a member selected from the group consisting of —C(O)— and —C(O)N($R^1$)—;
- $R^1$ is optionally substituted ($C_5$-$C_8$)cycloalkyl, optionally substituted phenyl, optionally substituted benzyl, and ($C_1$-$C_8$)alkyl; and
- $B^1$ and $B^2$ are each independently a member selected from the group consisting of optionally substituted ($C_5$-$C_8$) cycloalkyl, optionally substituted phenyl, and optionally substituted benzyl.

4. The compound of claim 1, wherein
- $A^1$ is a member selected from the group consisting of alkylene, arylene, and heteroarylene;
- $L^1$ and $L^2$ are each —C(O)N($R^1$)—;
- $R^1$ is a member selected from the group consisting of aryl, heteroaryl, and arylalkyl ; and
- $B^1$ and $B^2$ are each independently a member selected from the group consisting of aryl, heteroaryl, and cycloalkyl.

5. The compound of claim 1, wherein
- $A^1$ is a heteroarylene group containing two fused rings;
- $L^1$ and $L^2$ are each independently a member selected from the group consisting of —O—, —NH—, and —N($R^1$)—;
- $R^1$ is a member selected from the group consisting of alkyl and heteroalkyl; and
- $B^1$ and $B^2$ are each independently a member selected from the group consisting of aryl, heteroaryl, and cycloalkyl.

6. The compound of claim 1, wherein the compound is

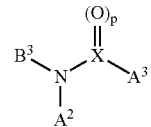

II

7. A pharmaceutical composition, said pharmaceutical composition comprising:
a) a compound of claim 1; and
b) a pharmaceutically acceptable carrier or excipient.

8. A pharmaceutical composition, said pharmaceutical composition comprising:
a) a compound of claim 5; and
b) a pharmaceutically acceptable carrier or excipient.

* * * * *

(12) EX PARTE REEXAMINATION CERTIFICATE (8576th)
United States Patent
Houze et al.

(10) Number: US 7,511,043 C1
(45) Certificate Issued: Sep. 27, 2011

(54) FXR MODULATORS

(75) Inventors: Jonathan Houze, San Mateo, CA (US); Sharon McKendry, San Francisco, CA (US); Joshua Gergely, San Francisco, CA (US); Yi Xia, South San Francisco, CA (US); Bei Shan, Redwood City, CA (US); Frank Kayser, San Francisco, CA (US)

(73) Assignee: Amgen Inc., Thousand Oaks, CA (US)

Reexamination Request:
No. 90/011,337, Dec. 20, 2010

Reexamination Certificate for:
Patent No.: 7,511,043
Issued: Mar. 31, 2009
Appl. No.: 10/794,228
Filed: Mar. 4, 2004

Related U.S. Application Data

(62) Division of application No. 09/945,293, filed on Aug. 31, 2001, now Pat. No. 6,777,446.
(60) Provisional application No. 60/258,092, filed on Dec. 22, 2000, and provisional application No. 60/230,585, filed on Sep. 5, 2000.

(51) Int. Cl.
*A61K 31/497* (2006.01)
*A61P 35/00* (2006.01)
*C07C 233/75* (2006.01)
*C07C 237/22* (2006.01)
*C07C 311/19* (2006.01)
*C07C 311/29* (2006.01)
*C07D 209/48* (2006.01)
*C07D 241/36* (2006.01)
*C07D 241/44* (2006.01)
*C07D 279/02* (2006.01)

(52) U.S. Cl. ............... 514/252.1; 544/353; 564/184
(58) Field of Classification Search ............... None
See application file for complete search history.

(56) References Cited

U.S. PATENT DOCUMENTS

| | | | |
|---|---|---|---|
| 4,167,567 A | 9/1979 | McCall |
| 4,252,804 A | 2/1981 | Joullier et al. |
| 4,594,373 A | 6/1986 | Kohli |
| 4,758,652 A | 7/1988 | Heitz et al. |
| 4,778,789 A | 10/1988 | Fex et al. |
| 4,829,061 A | 5/1989 | Wolf et al. |
| 5,708,172 A | 1/1998 | Oku et al. |

FOREIGN PATENT DOCUMENTS

| | | |
|---|---|---|
| EP | 0 264 865 | 4/1988 |
| EP | 0 436 734 | 7/1991 |
| JP | 53-31669 | 3/1978 |
| JP | 62-54084 | 11/1987 |
| JP | 7-252232 | 10/1995 |
| WO | WO 94/05628 | 3/1994 |
| WO | WO 96/34851 | 11/1996 |
| WO | WO 97/15576 | 5/1997 |
| WO | WO 98/35951 | 8/1998 |
| WO | WO 99/07672 | 2/1999 |

OTHER PUBLICATIONS

Akguen, et al., "Synthesis of Some Substituted Quinazolinediones as Potential Inhibitors of Smooth Muscle Contraction", Journal of Pharmaceutical Sciences, vol. 77, No. 9, pp. 735–739, 1988.
Compounds in Caplus (without bibliographic data), Nov. 16, 1984 (5 pp.).
Goldman, et al., "Anticonvulsants, Benzyl 4–Carbamyl–1–Piperazine–Carboxylate and Related Compounds", pp. 815–821, Jan. 9, 1953. J. Org. Chem. 18(7).
Nagasawa, et al., "Nj–Phenyl–1–thio–1,2–azetidinedicarboximide, the Phenylthiohydantoin of Azetidine–2–carboxylic Acid", J. Org. Chem., vol. 37, No. 3, pp. 516–519, 1972.
Cantor, m–Dibenzylbenzene, Journal of Chemical and Engineering Data, vol. 8, No. 3, pp. 459, Jul. 1963.

*Primary Examiner*—Gary Kunz

(57) ABSTRACT

The present invention provides compounds, pharmaceutical compositions and methods that are useful in modulating the farnesoid X receptor (FXR). As FXR is involved in negatively controlling the expression level of cholesterol 7α-hydroxylase (cyp7a), the rate-limiting enzyme involved in the oxidative metabolism of cholesterol into bile acids, the compounds described herein find utility in treating diseases associated with abnormally high or low cholesterol levels. In certain aspects, the FXR modulators (e.g., antagonists) described herein block the negative feed-back downregulation of cyp7a expression produced by certain cholic acids, the endogenous ligands for FXR. Moreover, as FXR forms heterodimers with the retinoid X receptor (RXR) in some cell types, modulation of the level of FXR activity in cells has a wide range of effects on a variety of biological processes which are mediated by RXR or other RXR-interacting proteins such as PPARγ and PPARα. Thus, compounds described herein are useful in treating other biological activities such as obesity, diabetes, lipid associated disorders, cancer, inflammatory disorders, disorders involving a disrupted or dysfunctional epidermal barrier, and various other metabolic disorders.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-5, 7 and 8 are cancelled.
Claim 6 was not reexamined.

* * * * *